US012644098B2

(12) United States Patent (10) Patent No.: US 12,644,098 B2
Li et al. (45) Date of Patent: Jun. 2, 2026

(54) HUMAN PLURIPOTENT ADULT STEM CELLS

(71) Applicant: APstem Therapeutics, Inc., Fremont, CA (US)

(72) Inventors: Shaowei Li, Newark, CA (US); Min Hu, Newark, CA (US); Bowen Liu, Union City, CA (US)

( * ) Notice: Subject to any disclaimer, the term of this patent is extended or adjusted under 35 U.S.C. 154(b) by 457 days.

(21) Appl. No.: 18/502,610

(22) Filed: Nov. 6, 2023

(65) Prior Publication Data

US 2024/0076610 A1 Mar. 7, 2024

Related U.S. Application Data

(63) Continuation of application No. 16/579,235, filed on Sep. 23, 2019, now Pat. No. 11,845,956.

(60) Provisional application No. 62/734,740, filed on Sep. 21, 2018.

(51) Int. Cl.
*C12N 5/074* (2010.01)

(52) U.S. Cl.
CPC ...... *C12N 5/0607* (2013.01); *C12N 2501/599* (2013.01)

(58) Field of Classification Search
None
See application file for complete search history.

(56) References Cited

U.S. PATENT DOCUMENTS

| | | | |
|---|---|---|---|
| 9,657,267 B2 | 5/2017 | Izadyar et al. | |
| 2006/0205075 A1* | 9/2006 | Nakatsuji | C12N 5/067 435/370 |
| 2009/0155226 A1 | 6/2009 | Kong et al. | |
| 2010/0227396 A1* | 9/2010 | Lim | C12N 5/0696 435/352 |
| 2011/0033428 A1 | 2/2011 | Maruyama et al. | |
| 2013/0280219 A1 | 10/2013 | Shiels | |
| 2016/0097036 A1 | 4/2016 | Chaurasia | |

FOREIGN PATENT DOCUMENTS

| | | |
|---|---|---|
| CN | 102884177 A | 1/2013 |
| CN | 106659560 A | 5/2017 |
| JP | 2011519574 A | 7/2011 |
| JP | 2013514760 A | 5/2013 |
| JP | 2014 073084 A | 4/2014 |
| WO | WO03026584 A2 | 4/2003 |
| WO | WO 2007118680 A2 | 10/2007 |
| WO | WO 2017115268 A1 | 7/2017 |
| WO | WO 2017176267 | 10/2017 |
| WO | WO 2017218846 | 12/2017 |
| WO | WO 2018187298 | 10/2018 |

OTHER PUBLICATIONS

Ding et al., "ABCG2: A potential marker of stem cells and novel target in stem cell and cancer therapy," Life Sciences, 2010, vol. 86, Issues 17-18, pp. 631-637.

Hu et al., "Expansion and Hepatic Differentiation of Adult Blood-Derived CD344 Progenitor Cells and Promotion of Liver Regeneration After Acute Injury," Stem Cells Translational Medicine, 2016, vol. 5, pp. 723-732.

Krebsbach, Paul H., et al: "The Role of Integrin a6 (CD49f) in Stem Cells: More than a Conserved Biomarker" Stem Cells and Development, vol. 26, No. 15, Aug. 1, 2017, pp. 1090-1099, xp055920751, DOI: 10.1089/scd.2016.0319 (10 pages).

Li Qiuhui et al: "Cancer stem cells and cell size: A causal link?" Seminars in Cancer Biology, vol. 35, Dec. 1, 2015, pp. 191-199, doi.org/10.1016/j.semcancer.2015.07.002, (25 pages).

Nakamura et al., "Angiopoietin-1 supports induction of hematopoietic activity in human CD34-bone marrow cells," Experimental Hematology, 2007, vol. 35, No. 12, pp. 1872-1883.

Bahlmann et al., "Erythropoietin regulates endothelial progenitor cells," Blood, 2004, vol. 103, No. 3, pp. 921-926.

Dupas et al., "Fetal muscle contains different CD34+ cell subsets that distinctly differentiate into adipogenic, angiogenic and myogenic lineages," Stem Cell Research, 2011, vol. 7, Issue 3, pp. 230-243.

European Search Report, dated Feb. 23, 2023, regarding Application No. 22197806. 7, 11 pages.

Kucia et al., "A population of very small embryonic-like (VSEL) CXCR4+SSEA-1+Oct-4+ stem cells identified in adult bone marrow," Stem Cells, 2006, vol. 20, pp. 857-869.

Li et al., "Treatment of Full-Thickness Skin Wounds with Blood-Derived CD34+ Precursor Cells Enhances Healing with Hair Follicle Regeneration," Advances in Wound Care, 2019, vol. 9, No. 5, pp. 264-276.

Park et al., "Human embryonic stem cell-derived hematoendothelial progenitors engraft chicken embryos," Experimental Hematology, 2009, vol. 37, Issue 1, pp. 31-41.

Invitrogen by Thermo Fisher Scientific 1x RBC Lysis Buffer pp. 1-2; downloaded Jan. 10, 2023.

Li et al., Peripheral Blood-Derived Mesenchymal Stem Cells: Candidate Cells Responsible for Healing Critical-Sized Calvarial Bone Defects Stem Cells Translationalmedicine 2015;4:359-368.

Extended Eurpoean Search Report, dated Sep. 30, 2022, regarding Application No. 19862488.4, 16 pages.

International Search Report and Written Opinion for PCT/US2019/052368 dated Dec. 4, 2019, 12 pages.

(Continued)

*Primary Examiner* — Tracy Vivlemore
*Assistant Examiner* — Fatimah Khalaf Matalkah

(57) ABSTRACT

Certain populations of small cells present in adult human tissue can undergo activation/development to form human pluripotent stem cell populations. These small cells are generally less than six micrometers in diameter and are CD49f-positive, and are referred to herein as human early stage precursors or CD49f+ cells. Accordingly, provided are cell populations and compositions with enriched CD49f+ cells from adult human tissue samples and methods and compositions for promoting activation/development of these CD49f+ cells. Upon differentiation, the activated stem cells can be used for various therapeutic purposes.

17 Claims, 6 Drawing Sheets

(56) References Cited

OTHER PUBLICATIONS

Ono et al., "CD34 and CD49f Double-Positive and Lineage Marker-Negative Cells Isolated from Human Myometrium Exhibit Stem Cell-Like Properties Involved in Pregnancy-Induced Uterine Remodelin", Biolo of Re roduction, Jun. 24, 2015, vol. 93, No. 2, Pa es 1-9.

Zeng et al., "Lack of ABCG2 expression and side population properties in human pluripotent stem cells", Stem Cells, Aug. 7, 2009, vol. 27, Issue 10, pp. 2435-2445.

* cited by examiner

HUMAN PLURIPOTENT ADULT STEM CELLS

CROSS REFERENCE TO RELATED APPLICATIONS

This application is a continuation of U.S. patent application Ser. No. 16/579,235, filed Sep. 23, 2019, which claims the benefit under 35 U.S.C. § 119(e) of the U.S. Provisional Application Ser. No. 62/734,740, filed Sep. 21, 2018, the content of each of which is incorporated by reference in its entirety into the present disclosure.

BACKGROUND

Stem cell-based therapies hold tremendous promise for the treatment of serious diseases and injuries. The ability of stem cells to self-renew and their capacity for differentiation offers significant potential to aid the repair, replacement, or regeneration of damaged cells, tissues, or organs. Currently various types of stem cells are investigated in preclinical and clinical studies, including embryonic stem cells (ESCs), stem cells isolated from adult tissues (e.g., mesenchymal stem cells (MSCs), Hematopoietic stem cells (HSCs), etc.), induced pluripotent stem cells (iPS cells or iPSCs), and a variety of specialized cells obtained by differentiation from the above cell sources among others.

Pluripotent stem cells offer various advantages over other sources of multipotent or unipotent somatic stem cells because of their robust self-renewal capacity in vitro and "pluripotency", which is the ability to differentiate into derivatives of the three embryonic germ layers. Current examples of pluripotent stem cells include ESCs and iPSCs. With respect to human ESCs, many problems have hindered their use in cell therapy, such as ethical issues, tumorigenicity, and immune-rejection because it has not been feasibility to produce patient-matched ESCs. Although some of these problems, such as the ethical issues and immuno-rejection, may be avoided by iPSCs that are derived directly from the patient's own cells, the tumorigenicity and low frequency of iPSCs derivation is still unresolved. Consequently, an unmet need resides in stem cell therapy for a source of human pluripotent stem cells derived from adult tissue with desired safety, efficacy, and feasibility of culture expansion for clinical use.

One of the major challenges for stem cell therapy is to translate the studies of stem cells using animal models to humans. For example, mouse ESCs were first isolated and studied in mice in the early '80s, while not until 1998 did a breakthrough occur when researchers first developed a technique to isolate and grow human embryonic stem cells in vitro. Although mice are considered to be the most important model organism for research into human biology, stem cells in mice and human may differ enormously. Fundamental differences exist in the molecular signatures, signaling pathways, colony shape, growth rate, surface markers, and developmental potential between mouse ESCs and human ESCs.

Therefore, there is a need for identification of human pluripotent stem cells isolated from adult human tissue, which can expand in vitro, have high efficiency in differentiation, and are non-tumorigenic. There is also a need for the establishment of a protocol for culturing these human pluripotent stem cells in vitro for cell-based therapy. Such pluripotent stem cells isolated from adult human tissue will pave the way for practical cell-based therapy for the treatment of tissue damages as well as chronic and aging related diseases.

SUMMARY

The identification of expandable, pluripotent stem cells from adult human tissue and the establishment of a protocol for culturing them in vitro will pave the way for practical cell-based therapy for the treatment of tissue damages as well as chronic and aging related diseases.

The present disclosure provides a method of preparing a cell population that comprises (1) removing at least a portion of red blood cells from a blood sample; (2) centrifuging the sample at 3,000×g-15,000×g and obtaining a pellet, (3) suspending cells in the pellet in a solution; and (4) enriching CD49f$^+$ cells in the solution. In some embodiments, at least 40% of the cells in the solution are CD49f$^+$ cells that express CD49f and have a diameter of less than 6 μm. In some aspects, the sample is centrifuged at more than 5,000×g, 6,000×g, or 7,000×g. In some aspects, the CD49f$^+$ cells are further characterized as positive in SSEA4. In some aspects, the CD49f$^+$ cells are further characterized as negative in ABCG2 and Lin. In some aspects, the CD49f$^+$ cells are further characterized as positive in CD73 and CD45, and negative in CD4 and Lin28. In some aspects, the CD49f$^+$ cells further express one or more markers selected from the group consisting of Oct4, Nanog, CD31, CD117, and CD105. In some aspects, the CD49f$^+$ cells do not express one or more markers selected from the group consisting of CD3, CD4, CD8, CD11b, and CD41. In some aspects, less than 20% of the cells are red blood cells.

Also provided is a composition comprising at least 1000 cells, and at least 40% of the cells are CD49f$^+$ cells that express CD49f and have a diameter of less than 6 μm. In some aspects, the CD49f$^+$ cells are further characterized as positive in SSEA4. In some aspects, the CD49f$^+$ cells are further characterized as negative in ABCG2 and Lin. In some aspects, the CD49f$^+$ cells are further characterized as positive in CD73 and CD45, and negative in CD4 and Lin28. In some aspects, the CD49f$^+$ cells further express one or more markers selected from the group consisting of Oct4, Nanog, CD31, CD117, and CD105. In some aspects, the CD49f$^+$ cells do not express one or more markers selected from the group consisting of CD3, CD4, CD8, CD11b, and CD41. In some aspects, less than 20% of the cells are red blood cells. In some aspects, the CD49f$^+$ cells can be activated by a medium comprising one or more factors, and the activated cells express ABCG2.

Also provided is method of culturing cells, comprising culturing a plurality of human cells in a medium that is in contact with or has been conditioned with at least one selected from the group consisting of primary hepatocytes and hepatic cell lines. In some aspects, the hepatic cell lines comprise cell lines derived from hepatomas, immortalized hepatocytes, immortal hepatocytes isolated from transgenic animals, hepatocyte/hepatoma hybrid cells, genetically engineered hepatocytes, hepatic progenitor cells, or the combination thereof. In some aspects, the human cells (a) have a diameter of less than 6 μm, and (b) are CD49f$^+$ cells. In some aspects, the CD49f$^+$ cells are further characterized as positive in SSEA4. In some aspects, the CD49f$^+$ cells are further characterized as negative in ABCG2 and Lin. In some aspects, the cells, following the culturing, express ABCG2. In some aspects, the human cells include one or more types of stem cells.

The present disclosure further provides an isolated human cell that expresses CD49f and does not express Lin. In some aspects, the human cell is further characterized as positive in ABCG2. In some aspects, the human cell is further characterized as positive in SSEA4. In some aspects, the human cell is further characterized as positive in Oct4, Nanog, Lin 28, CD73, and CD105. In some aspects, the human cell does not express CD45, CD14 and/or CD19. In some aspects, the human cell, after being cultured in a medium comprising one or more factors for a period of time, develops into a colony. Also provided is a population of the cells as disclosed herein.

Also provided is a stem cell derived from a population of human cells that (a) have a diameter of less than 6 µm, (b) expresses CD49f, and (c) does not express ABCG2, wherein the population of stem cells expresses ABCG2, and is a heterogenous cell population. The embodiments of the disclosure also provide a cell differentiated from the stem cell as disclosed herein.

Also provided is a composition comprising at least 1000 cells, and at least 40% of the cells expresses CD49f and ABCG2, and does not express Lin. In some aspects, the at least 40% of the cells are further characterized as positive in CD73 and/or SSEA4. In some aspects, the at least 40% of the cells are further characterized as positive in Oct4, Nanog, and/or CD105.

Also provided is a composition comprising the early stage precursors and/or stem cells, as disclosed herein, in a pharmaceutically acceptable carrier or excipient. In some embodiments, also provided is a composition comprising the differentiated cells, as disclosed herein, in a pharmaceutically acceptable carrier or excipient. Also provided is a method of treating a disease or condition in a subject in need thereof, comprising administering an effective amount of the composition as disclosed herein to the subject.

DETAILED DESCRIPTION

Figure 1:
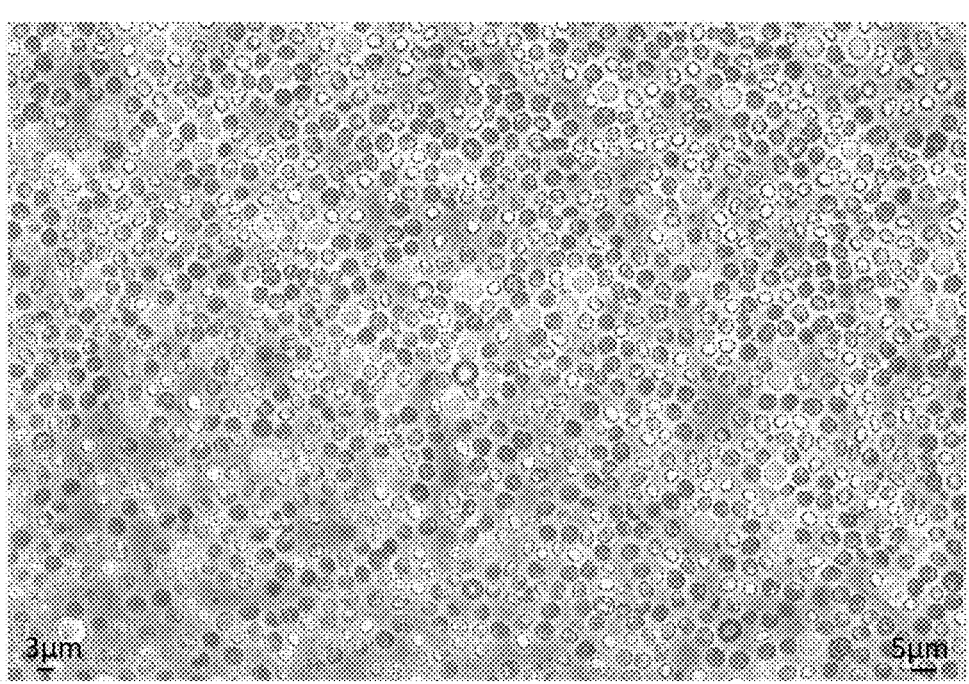
FIG. 1 shows a microscope image of a cell population that includes early stage precursors isolated from human peripheral blood.

Throughout this disclosure, various publications, patents and published patent specifications are referenced herein. The disclosures of these publications, patents and published patent specifications are hereby incorporated by reference in their entirety into the present disclosure.

Before the compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, $3^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, $3^{rd}$ edition (Cold Spring Harbor Laboratory Press (2002)); Current Protocols In Molecular Biology (F. M. Ausubel, et al. eds., (1987)); the series Methods in Enzymology (Academic Press, Inc.): PCR 2: A Practical Approach (M. J. MacPherson, B. D. Hames and G. R. Taylor eds. (1995)); Harlow and Lane, eds. (1988) Antibodies, A Laboratory Manual; Harlow and Lane, eds. (1999) Using Antibodies, A Laboratory Manual; Animal Cell Culture (R.I. Freshney, ed. (1987)); Zigova, Sanberg and Sanchez-Ramos, eds. (2002) Neural Stem Cells.

All numerical designations, e.g., pH, temperature, time, concentration, and molecular weight, including ranges, are approximations which are varied (+) or (−) by increments of 0.1 or 1 where appropriate. It is to be understood, although not always explicitly stated that all numerical designations are preceded by the term "about". The term "about" also includes the exact value "X" in addition to minor increments of "X" such as "X+0.1 or 1" or "X−0.1 or 1", where appropriate. It is also to be understood, although not always explicitly stated, that the reagents described herein are merely exemplary and that equivalents of such are known in the art.

1. Definitions

Unless defined otherwise, all technical and scientific terms used herein have the same meaning as commonly understood by one of ordinary skill in the art to which this disclosure belongs. As used herein the following terms have the following meanings.

As used in the specification and claims, the singular forms "a", "an", and "the" include plural referents unless the context clearly dictates otherwise. Thus, for example, reference to "a cell" includes a plurality of cells, including mixtures thereof.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) claimed. "Consisting of" shall mean excluding more than trace elements of other ingredients and substantial method steps. Embodiments defined by each of these transition terms are within the scope of this disclosure.

As used herein, the term "isolated" means separated from constituents, cellular and otherwise, in which the cell, tissue, polynucleotide, peptide, polypeptide, protein, antibody or fragment(s) thereof, which are normally associated in nature. For example, an isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart. An isolated cell is a cell that is separated from tissue or cells of dissimilar phenotype or genotype.

As used herein, "stem cell" defines a cell with the ability to divide for indefinite periods in culture and give rise to specialized cells. Non-limiting examples of types of stem cells include somatic (adult) stem cells, embryonic stem cells, parthenogenetic stem cells (see Cibelli et al. (2002) Science 295(5556):819; U.S. Patent Publ. Nos. 20100069251 and 20080299091), and/or induced pluripotent stem cells (iPS cells or iPSCs). A somatic stem cell is an undifferentiated cell found in a differentiated tissue that can renew itself (clonal) and (with certain limitations) differentiate to yield all the specialized cell types of the tissue from which it originated. An embryonic stem cell is a primitive (undifferentiated) cell from the embryo that has the potential to become a wide variety of specialized cell types. Non-limiting examples of embryonic stem cells include the HES2 (also known as ES02) cell line available from ESI, Singapore and the H1 or H9 (also known as WA01) cell line available from WiCell, Madison, WI. Additional lines are pending NIH review. See, for example, grants.nih.gov/stem cells/registry/current.htm (last accessed Mar. 13, 2017). Pluripotent embryonic stem cells can be distinguished from other types of cells by the use of markers including, but not limited to, Oct4, alkaline phosphatase, CD30, TDGF-1, GCTM-2, Genesis, Germ cell nuclear factor, SSEA1, SSEA3, and SSEA4. An induced pluripotent stem cell (iPSC) is an artificially derived stem cell from a non-pluripotent cell, typically an adult somatic cell, produced by inducing expression of one or more stem cell specific genes. An iPSC expresses specific genes including, but are not limited to, the family of octamer transcription factors, e.g., Oct-3/4; the family of Sox genes, e.g., Sox1, Sox2, Sox3, Sox 15 and Sox 18; the family of Klf genes, e.g., Klf1, Klf2, Klf4 and Klf5; the family of Myc genes, e.g., c-myc and L-myc; the family of Nanog genes, e.g., Octamer-4 (OCT4), NANOG and REX1; or LIN28. Examples of iPSCs are described in Takahashi et al. (2007) Cell advance online publication 20 Nov. 2007; Takahashi & Yamanaka (2006) Cell 126:663-76; Okita et al. (2007) Nature 448:260-262; Yu et al. (2007) Science advance online publication 20 Nov. 2007; and Nakagawa et al. (2007) Nat. Biotechnol. Advance online publication 30 Nov. 2007.

As used herein, the term "propagate" means to grow or alter the phenotype of a cell or population of cells. The term "grow" or "expand" refers to the proliferation of cells in the presence of supporting media, nutrients, growth factors, support cells, or any chemical or biological compound necessary for obtaining the desired number of cells or cell type. In one embodiment, the growing/expansion of cells results in the regeneration of tissue.

As used herein, the term "culturing" refers to the in vitro propagation of cells or organisms on or in media of various kinds. It is understood that the descendants of a cell grown in culture may not be completely identical (i.e., morphologically, genetically, or phenotypically) to the parent cell. By "expanded" is meant any proliferation or division of cells.

As used herein and as set forth in more detail below, "conditioned medium" is medium which was cultured with a mature cell that provides cellular factors to the medium such as cytokines, growth factors, hormones, extracellular matrix, and some materials that would facilitate cell growth, development, and differentiation.

As used herein, the term "differentiation" describes the process whereby an unspecialized cell acquires the features of a specialized cell such as a skin, heart, liver, or muscle cell. "Directed differentiation" refers to the manipulation of stem cell culture conditions to induce differentiation into a particular cell type. "Dedifferentiated" defines a cell that reverts to a less committed position within the lineage of a cell. As used herein, the term "differentiates or differentiated" defines a cell that takes on a more committed ("differentiated") position within the lineage of a cell.

As used herein, the "lineage" of a cell defines the heredity of the cell, i.e. its predecessors and progeny. The lineage of a cell places the cell within a hereditary scheme of development and differentiation. As used herein, "a cell that differentiates into a mesodermal (or ectodermal or endodermal) lineage" defines a cell that becomes committed to a specific mesodermal (or ectodermal or endodermal) lineage, respectively. Examples of cells that differentiate into a mesodermal lineage or give rise to specific mesodermal cells include, but are not limited to, cells that are adipogenic, leiomyogenic, chondrogenic, cardiogenic, dermatogenic, hematopoetic, hemangiogenic, myogenic, nephrogenic, urogenitogenic, osteogenic, pericardiogenic, or stromal. Examples of cells that differentiate into ectodermal lineage include, but are not limited to epidermal cells, neurogenic cells, and neurogliagenic cells. Examples of cells that differentiate into endodermal lineage include, but are not limited to cells that give rise to the pancreas, liver, lung, stomach, intestine, and thyroid.

As used herein, the term "pluripotent stem cells" refers to cells that are: (i) capable of indefinite proliferation in vitro in an undifferentiated state; (ii) maintain a normal karyotype through prolonged culture; and (iii) maintain the potential to differentiate to derivatives of all three embryonic germ layers (endoderm, mesoderm, and ectoderm) even after prolonged culture. Non-limiting examples of currently available pluripotent stem cells include embryonic stem cells and iPSCs. As used herein, the term "embryonic-like stem cells" refers to cells derived from tissues, organs, or blood, possessing pluripotent characteristics of embryonic stem cells.

As used herein, the term "multi-lineage stem cell" or "multipotent stem cell" refers to a stem cell that reproduces itself and at least two further differentiated progeny cells from distinct developmental lineages. The lineages can be from the same germ layer (i.e. mesoderm, ectoderm, or endoderm), or from different germ layers. An example of two progeny cells with distinct developmental lineages from differentiation of a multi-lineage stem cell is a myogenic cell and an adipogenic cell (both are of mesodermal origin, yet give rise to different tissues). Another example is a neurogenic cell (of ectodermal origin) and adipogenic cell (of mesodermal origin).

As used herein, the term "self-renewable" refers to a cell being able to self-renew for over a number of passages without substantial changes of cell properties. In one aspect, the number of passages is at least about 2, or alternatively at least 5, or alternatively at least 10, or alternatively at least about 15, 20, 30, 50, or 100.

As used herein, the term "substantially homogeneous" describes a population of cells in which more than about 50%, or alternatively more than about 60%, or alternatively more than 70%, or alternatively more than 75%, or alternatively more than 80%, or alternatively more than 85%, or alternatively more than 90%, or alternatively more than 95%, or alternatively more than 99% of the cells are of the same or similar phenotype. Phenotype can be determined by a pre-selected cell surface marker or other marker.

As used herein, the term "purified population" of cells of interest refers to the cell population that has been isolated away from substantially all other cells that exist in their native environment, but also when the proportion of the cells of interest in a mixture of cells is greater than would be found in their native environment. For example, a purified population of cells represents an enriched population of the cells of interest, even if other cells and cell types are also present in the enriched population. In some embodiments, a purified population of cells represents at least about 10%, at least about 20%, at least about 30%, at least about 40%, at least about 50%, at least about 60%, at least about 70%, at least about 80%, at least about 90%, at least about 95%, at least about 99%, or about 100% of a mixed population of cells, with the proviso that the cells of interest comprise a greater percentage of the total cell population in the "purified" population than they did in the population prior to purification.

As used herein, the term "population of cells" refers to a collection of more than one cell that is identical (clonal) or non-identical in phenotype and/or genotype.

As used herein, the term "cell colony" or "colony" refers to a grouping of closely associated cells formed as a result of cell growth. These terms are used irrelevantly to the number of cells constituting the colony.

As used herein, the term "dormant" or "quiescent," as used herein, is intended to encompass cells that are in a state which are required to be activated before they can undergo growth, division, and/or differentiation.

As used herein, the term "precursors" or "precursor cells" is intended to encompass cells that can give rise to one or more specific types of cells. As used herein, the term "early stage precursors" is intended to encompass precursor cells that express certain early stage markers. In some embodiments, the early stage precursors, upon activation/development, give rise to one or more populations of stem cells. In some embodiments, the early stage precursors remain in dormant/quiescent state prior to activation/development.

As used herein, the term "activation" or "development" of cells refers to a measurable morphological, phenotypic, and/or functional change in the dormant/quiescent state of the cells. Such activation/development is typically concurrent with the expression of specific markers for the activated cells. In one embodiment, activation/development is concurrent with a change in cell growth, division, and/or development. In some embodiments, activation/development of the early stage precursors includes cell fusion, mixing of cytoplasmic and/or genetic material, nuclear transfer, genetic material exchange, reprograming, and/or formation of hybrid cells.

As used herein, the term "activated stem cells" is intended to encompass stem cells that are in an activated state and can undergo growth, division, and/or differentiation under specific conditions.

As used herein, the term "composition" is intended to encompass a combination of active agent and another carrier, e.g., compound or composition, inert (for example, a detectable agent or label) or active, such as an adjuvant, diluent, binder, stabilizer, buffers, salts, lipophilic solvents, preservative, adjuvant or the like. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol. In certain embodiments, a composition includes a population of cells or a mixture of cells. In certain embodiments, the composition is formulated as a film, gel, patch, 3-D structure, or liquid solution.

As used herein, the term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile.

As used herein, the term "pharmaceutically acceptable carrier (or medium)", which may be used interchangeably with the term "biologically compatible carrier (or medium)", refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio. Pharmaceutically acceptable carriers suitable for use in the present invention include liquids, semi-solid (e.g., gels) and solid materials (e.g., cell scaffolds and matrices, tubes sheets and other such materials as known in the art and described in greater detail herein). These semi-solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways. For topical use, the pharmaceutically acceptable carrier is suitable for manufacture of creams, ointments, jellies, gels, solutions, suspensions, etc. Such carriers are conventional in the art, e.g., for topical administration with polyethylene glycol (PEG). These formulations may optionally comprise additional pharmaceutically acceptable ingredients such as diluents, stabilizers, and/or adjuvants.

As used herein, the term "solution" refers to solutions, suspensions, emulsions, drops, ointments, liquid wash, sprays, and liposomes, which are well known in the art. In some embodiments, the liquid solution contains an aqueous pH buffering agent which resists changes in pH when small quantities of acid or base are added.

As used herein, the term "pH buffering agent" refers to an aqueous buffer solution which resists changes in pH when small quantities of acid or base are added to it. pH buffering solutions typically comprise a mixture of weak acid and its conjugate base, or vice versa. For example, pH buffering solutions may comprise phosphates such as sodium phosphate, sodium dihydrogen phosphate, sodium dihydrogen phosphate dihydrate, disodium hydrogen phosphate, disodium hydrogen phosphate dodecahydrate, potassium phosphate, potassium dihydrogen phosphate and dipotassium hydrogen phosphate; boric acid and borates such as, sodium borate and potassium borate; citric acid and citrates such as sodium citrate and disodium citrate; acetates such as sodium acetate and potassium acetate; carbonates such as sodium carbonate and sodium hydrogen carbonate, etc. pH adjusting agents can include, for example, acids such as hydrochloric acid, lactic acid, citric acid, phosphoric acid and acetic acid, and alkaline bases such as sodium hydroxide, potassium hydroxide, sodium carbonate and sodium hydrogen carbonate, etc. In some embodiments, the pH buffering agent is a phosphate buffered saline (PBS) solution (i.e., containing sodium phosphate, sodium chloride and in some formulations, potassium chloride and potassium phosphate).

As used herein, the term "formulated" or "formulation" refers to the process in which different substances, including one or more pharmaceutically active ingredients, are combined to produce a dosage form. In certain embodiments, two or more pharmaceutically active ingredients can be co-formulated into a single dosage form or combined dosage unit, or formulated separately and subsequently combined into a combined dosage unit. A sustained release formulation is a formulation which is designed to slowly release a therapeutic agent in the body over an extended period of time, whereas an immediate release formulation is a formulation which is designed to quickly release a therapeutic agent in the body over a shortened period of time.

As used herein, the term "treating" refers to preventing, curing, reversing, attenuating, alleviating, minimizing, inhibiting, suppressing and/or halting one or more clinical symptoms of a disease or disorder prior to, during, and/or after an injury or intervention.

As used herein, the term "patient" or "subject" refers to animals, including mammals, such as murine, canine, equine, bovine, porcine, simian, or humans, who are treated with the pharmaceutical compositions or in accordance with the methods described herein.

As used herein, the term "delivery" refers to routes, approaches, formulations, technologies, and systems for transporting a pharmaceutical composition in the body as needed to safely achieve its desired therapeutic effect. The route of delivery can be any suitable route, including but not limited to, intravascular, intravenous, intraarterial, intramuscular, cutaneous, subcutaneous, percutaneous, intradermal, and intraepidermal routes. In some embodiments, an effective amount of the composition is formulated for applying on the skin or delivery into the skin of a patient. In some embodiments, an effective amount of the composition is formulated for delivery into the blood stream of a patient.

As used herein, the term "effective amount" refers to a concentration or amount of composition or a reagent, such as a composition as described herein, cell population or other agent, that is effective for producing an intended result, including cell growth, cell division, and/or differentiation in vitro or in vivo, or for the treatment of a disease, disorder or condition in a patient in need thereof. It will be appreciated that the number of cells to be administered will vary depending on the specifics of the disorder to be treated, including but not limited to size or total volume/surface area to be treated, as well as proximity of the site of administration to the location of the region to be treated, among other factors familiar to the medicinal biologist and/or treating physician.

As used herein, the terms "effective period (or time)" and "effective conditions" refer to a period of time or other controllable conditions (e.g., temperature, humidity for in vitro methods), necessary or preferred for an agent or composition to achieve its intended result, e.g., the differentiation of cells to a pre-determined cell type.

As used herein, the term "control" or "control group" refers to an alternative subject or sample used in an experiment for comparison purpose. A control can be "positive" or "negative".

As used herein, the term "concurrently" refers to simultaneous (i.e., in conjunction) administration. In one embodiment, the administration is co-administration such that two or more pharmaceutically active ingredients, including any solid form thereof, are delivered together at one time.

As used herein, the term "sequentially" refers to separate (i.e., at different times) administration. In one embodiment, the administration is staggered such that two or more pharmaceutically active ingredients, including any solid form thereof, are delivered separately at different times.

As used herein, the term "target tissue" or "target organ" refers to an intended site for accumulation of the stem cells as disclosed herein and/or the differentiated cells derived from the stem cells as disclosed herein, following administration to a subject. For example, the methods as disclosed herein involve a target tissue or a target organ that has been damaged (e.g., by ischemia or other injury) in some embodiments.

As used herein, the terms "autologous transfer", "autologous transplantation", "autograft" and the like refer to treatments wherein the cell donor is also the recipient of the cell replacement therapy. The terms "allogeneic transfer", "allogeneic transplantation", "allograft" and the like refer to treatments wherein the cell donor is of the same species as the recipient of the cell replacement therapy, but is not the same individual. A cell transfer in which the donor's cells have been histocompatibly matched with a recipient is sometimes referred to as a syngeneic transfer. The terms xenogeneic transfer, xenogeneic transplantation, xenograft and the like refer to treatments wherein the cell donor is of a different species than the recipient of the cell replacement therapy.

As used herein, the term "Oct4," "Oct3/4," or "octamer-binding transcription factor 4" refers to a member of the octamer transcription factor family and is frequently used as a marker for undifferentiated cells, and having the gene symbol POU5F1. Oct4 is also known as Pou5f1 (POU domain, class 5, transcription factor 1, van Eijk et a., 1999). The GENBANK® database discloses amino acid and nucleic acid sequences of Oct4 from humans (e.g., NM_002701.5), mice (NM_013633.3), rats (NM_001009178.2), cats (NM_001173441.1), cows (NM_174580.3), and others.

As used herein, the term "ABCG2" or "ATP binding cassette (ABC) transporter G2" refers to a half transporter of the ABCG family belonging to the ABCG/white subfamily, and having the gene symbol ABCG2. ABCG2 is also known as CD338 or CDw338 (cluster of differentiation w338, Leccia et al., 2014), MXR (Mitoxantrone Resistance protein, Miyake et al., 1999), BCRP (Breast Cancer Resistance Protein, Doyle et al., 1998), or ABCP (placenta specific ABC transporter, Allikmets et al., 1998). The GENBANK® database discloses amino acid and nucleic acid sequences of ABCG2 from humans (e.g., AAG52982), mice (NM_011920.3), rats (BAC76396.1), cats (XP_019684813.1), dogs (NP_001041486.1), pigs (NP_999175.1), cows (NP_001032555.2), and others.

As used herein, the term "CD49f" refers to a member of the integrin alpha chain family of proteins, and having the gene symbol ITGA6. CD49f is also known as ITGA6 or ITGA6B (Integrin Subunit Alpha 6, Cariati et al., 2008), or VLA-6 (Hemler et al., 1989). The GENBANK® database discloses amino acid and nucleic acid sequences of CD49f from humans (e.g., NM_001079818.2), mice (NM_008397.4), rats (NM_053725.1), cows (NM_001109981.1), and others.

As used herein, the term "CD34" refers to a cell surface marker found on certain hematopoietic and non-hematopoietic stem cells, and having the gene symbol CD34. The GENBANK® database discloses amino acid and nucleic acid sequences of CD34 from humans (e.g., AAB25223), mice (NP_598415.1), rats (NP_001100672.1), cats (NP_001009318.1), pigs (NP_999251.1), cows (NP_776434.1), and others.

As used herein, the term "CD117" refers to a cytokine receptor expressed on the surface of hematopoietic stem cells as well as other cell types, and having the gene symbol KIT. CD117 is also known as KIT (Giebel et al., 1991), c-Kit (Yarden et al., 1987), PBT (Piebald trait protein, Fleischman et al., 1991), or SCFR (mast/stem cell growth factor receptor, Spritz, et al., 1992). The GENBANK® database discloses amino acid and nucleic acid sequences of CD117 from humans (e.g., NM_000222.2), mice (NM_001122733.1), rats (NM_022264.1), cats (NM_001009837.3), dogs (NM_001003181.1), pigs (NM_001044525.1), and others.

As used herein, the term "CD184" refers to an alpha-chemokine receptor specific for stromal-derived-factor-1 (SDF-1, also called CXCL12), and having the gene symbol CXCR4. CD184 is also known as CXCR4 (C-X-C chemokine receptor type 4, Endres et al., 1996), LAP 3 or LAP-3 (Lipopolysaccharide Associated Protein 3, Kageyama et al., 2008), or Fusin (Dimitrov, 1996). The GENBANK® database discloses amino acid and nucleic acid sequences of CD184 from humans (e.g., AJ224869.1), mice (BC098322.1), rats (NM_022205.3), cats (NM_001009826.1), dogs (NM_001048026.1), pigs (DQ124104.1), cows (NM_174301.3), and others.

As used herein, the term "CD45" refers to a tyrosine phosphatase, and having the gene symbol PTPRC. CD45 is also known as PTPRC (Protein tyrosine phosphatase, receptor type C, Goff et al., 1999), or L-CA or LCA (leukocyte-common antigen, Pingel et al., 1989). This gene corresponds to GENBANK® Accession Nos. NP_002829 (human), NP_035340 (mouse), NP_612516 (rat), XP_002829 (dog), XP_599431 (cow), and AAR16420 (pig). The amino acid sequences of additional CD45 homologs are also present in the GENBANK® database, including those from several fish species and several non-human primates. Various isoforms of CD45 exist, e.g., CD45RA, CD45RB, CD45RC, CD45RAB, CD45RAC, CD45RBC, CD45RO, and CD45R (ABC).

As used herein, the term "lineage markers" or "Lin" refers to characteristic molecules for cell lineages, e.g. cell surface markers, mRNAs, or internal proteins. Lineage-positive (Lin$^+$) cells refer to a mix of cells expressing mature cell lineage markers. Lineage-negative (Lin$^-$) cells include stem and progenitor cells, which are not differentiated mature cells. In one aspect, "Lin" refers to a panel of markers. As used herein, the FITC anti-human lineage antibody cocktail is optimized for the detection of human peripheral blood T cells, B cells, NK cells, monocytes, and neutrophils. This cocktail is composed of CD3, CD14, CD16, CD19, CD20, and CD56.

As used herein, the term "hepatic cell lines" refers to cell lines derived from liver. Non-limiting examples of hepatic cell lines include cell lines derived from hepatomas, immortalized hepatocytes, immortal hepatocytes isolated from transgenic animals, hepatocyte/hepatoma hybrid cells, genetically engineered hepatocytes, hepatic progenitor cells, or the combination thereof. In one aspect, cell lines derived from hepatomas may include, but are not limited to, HepG2, HepG2.2.15, HLE, HLF, HuH-7, Hep3B, PLC/PRF-5, SNU182, SNU354, SNU368, SNU387, SNU398, SNU423, SNU449, SNU475, and HepaRG. In another aspect, hepatic cell lines may also be generated via immortalization of hepatocytes. In one embodiment, immortalized hepatocytes may include hepatocytes generated via transformation with virus genes or oncogenes (i.e., simian virus SV40 large T antigen, c-myc, cH-ras), or via transfection using recombinant plasmids. In another embodiment, immortal hepatocytes may be isolated from transgenic animals expressing viral transforming genes, oncogenes or growth factors. In yet another embodiment, hepatocyte/hepatoma hybrid cells may be generated that remain permanently growing while expressing adult hepatic enzymes. In another embodiment, hepatic cell lines also include genetically engineered hepatocytes expressing human drug-metabolizing enzymes. In another embodiment, hepatic cell lines also include hepatic progenitor cells, such as oval cells in the liver.

2. Isolation of Early Stage Precursors from Adult Human Tissue

Researchers have long been looking for sources of pluripotent stem cells from adult human tissue for potential clinical uses. The instant invention demonstrates that populations of early stage precursors having relatively small size could be isolated from adult human tissue. These early stage precursors could go through activation/development to become human pluripotent stem cells. The pluripotency is demonstrated with the cells' ability to be differentiated into all three germ layers. Further, with a new activation/development system developed herein, the human pluripotent stem cells can be obtained and expanded in vitro. Moreover, the pluripotent stem cells derived from adult human tissue are not considered ethically and politically controversial, and do not require genetic manipulation. Yet another advantage of the present technology is that the human pluripotent stem cells are demonstrated to be non-tumorigenic. Therefore, the presently disclosed technology will pave the way for practical cell-based therapy for the treatment of tissue damages as well as chronic and aging related diseases.

In one embodiment, this disclosure provides a composition or a cell population enriched with human cells that express CD49f and have a diameter of less than 6 μm. Such human cells are herein referred to as "CD49f+ cells" or "early stage precursors." In some embodiments, the composition or cell population includes a total of at least 100 cells, 1000 cells, 10,000 cells, 100,000 cells, or 1,000,000 cells, and at least about 30%, 35%, 40%, 45%, 50%, 55%, 60%, 65%, 70%, 75%, 80%, 85%, 90% or 95% of them are early stage precursors. In some embodiments, the composition or cell population enriched with early stage precursors are isolated from an adult tissue sample of a human subject. In some embodiments, the composition or cell population further includes cells other than the early stage precursors, at a percentage of less than about 70%, 65%, 60%, 55%, 50%, 45%, 40%, 35%, 30%, 25%, 20%, 15%, 10% or 5%. In some embodiments, the composition or cell population enriched with early stage precursors are isolated from a blood sample of a human subject. In some embodiments, the composition further includes blood cells, such as red blood cells and white blood cells. In some embodiments, the composition or cell population enriched with early stage precursors includes blood cells at a percentage of less than about 70%, 65%, 60%, 55%, 50%, 45%, 40%, 35%, 30%, 25%, 20%, 15%, 10% or 5%.

In some embodiments, the early stage precursors in the composition include both intact and broken ones. In some embodiments, the ratio of the number of intact early stage precursors to the broken early stage precursors in the cell population is less than 1:1, at least about 1:1, 2:1, 3:1, 4:1, 5:1, 6:1, 7:1, 8:1, 9:1, 10:1, 11:1, 12:1, 13:1, 14:1, or 15:1.

In some embodiments, the human early stage precursors have a diameter of about 1 μm, or alternatively about 1.5 μm, or alternatively about 2 μm, or alternatively about 2.5 μm, or alternatively about 3 μm, or alternatively about 3.5 μm, or alternatively about 4 μm, or alternatively about 4.5 μm, or alternatively about 5 μm, or alternatively about 5.5 μm, or alternatively about 6 μm, or alternatively between about 1-2 μm, or alternatively between about 1-3 μm, or alternatively between about 1-4 μm, or alternatively between about 1-5 μm, or alternatively between about 1-6 μm, or alternatively between about 2-3 μm, or alternatively between about 2-4 μm, or alternatively between about 2-5 μm, or alternatively between about 2-6 μm, or alternatively between about 3-4 μm, or alternatively between about 3-5 μm, or alternatively between about 3-6 μm, or alternatively between about 4-5 μm, or alternatively between about 4-6 μm, or alternatively between about 5-6 μm, or alternatively less than 6 μm, or alternatively less than 5 μm, or alternatively less than 4 μm, or alternatively less than 3 μm, or alternatively less than 2 μm, or alternatively less than 1 μm. In some embodiments, the isolated human early stage precursors have very high nucleus-cytoplasm ratio (v/v, also referred to as N:C ratio, or N/C). In some embodiments, the nucleus/cytoplasm ratio of an early stage precursor as disclosed herein may be at least 9:1, or alternatively at least 8:1, or alternatively at least 7:1, or alternatively at least 6:1, or alternatively at least 5:1. In some embodiments, the percentage of the area of the cell occupied by the nucleus in an early stage precursor as disclosed herein may be at least 60%, or alternatively at least 70%, or alternatively at least 80%, or alternatively at least 90%, or alternatively at least 95%, or alternatively at least 98%. In some embodiments, the cytoplasm of an early stage precursor as disclosed herein may be minimal. When seeded in regular cell culture medium (e.g., α-MEM with 10% FBS) in vitro, in some embodiments, the human early stage precursors do not proliferate and become senescent in a few days.

In some embodiments, the isolated population of human early stage precursors is a heterogeneous cell mixture, including various sub-populations of cells characterized by different sets of markers. In some embodiments, the isolated population of human early stage precursors includes a sub-population of cells that express CD49f and/or SSEA4, and does not express ABCG2 and/or Lin. In some embodiments, the isolated population of human early stage precursors includes a sub-population of cells that express one or more markers selected from CD49f, SSEA4, CD117, Oct4, Nanog, CD45, and CD105. In some embodiments, the isolated population of human early stage precursors includes a sub-population of cells that express one or more markers selected from CD49f, CD31, SSEA4, CD117, Oct4, Nanog, CD45, and CD105. In some embodiments, the isolated population of human early stage precursors includes a sub-population of cells that express one or more markers selected from CD49f, CD73, CD31, SSEA4, CD117, Oct4, Nanog, CD184, CD45, and CD105. In some embodiments, the isolated population of human early stage precursors express very low level of CD34.

In some embodiments, the isolated population of human early stage precursors do not express the marker ABCG2 (CD338). In some embodiments, the human early stage precursors are further characterized to be Lin⁻. In some embodiments, the isolated population of human early stage precursors do not express one or more markers selected from CD90, Lin28, CD3, CD4, CD8, CD11b, CD14, CD19, and CD41.

The human early stage precursors may be analyzed using the cell surface markers and intracellular markers such as those shown in Table 1, below.

TABLE 1

| Antigen or Marker | Example GenBank Accession No. |
| --- | --- |
| CD49f (ITGA6) | NM_001079818.2 |
| CD34 | NM_001025109.1 |
| CD31 | NM_000442.5 |
| CD117 (c-KIT) | NM_000222.2 |
| CD45 (PTPRC) | NM_002838.4 |
| CD184 (CXCR4) | NM_001008540.2 |
| CD105 | NM_007932.2 |
| Oct4 | NM_002701.5 |
| Nanog | NM_024865.3 |
| ABCG2 (CD338) | NM_004827.2 |

In some embodiments, the human early stage precursors as disclosed herein express one or more early stage stem cell markers (e.g., Oct4, Nanog, and SSEA4). In some embodiments, the human early stage precursors as disclosed herein express one or more markers of the group of hematopoietic markers (e.g., CD117 and CD45). In some embodiments, the human early stage precursors as disclosed herein express one or more markers of the group of MSC markers (e.g., CD105 and CD73). In some embodiments, the human early stage precursors as disclosed herein express one or more proliferation markers (e.g., Cyclin D1$^{Low}$ and c-Myc). In some embodiments, the human early stage precursors as disclosed herein express one or more cytokines (e.g., VEGF and IL10). In some embodiments, the human early stage precursors as disclosed herein are HLA-I$^{Low}$/HLA-II$^-$. In some embodiments, the isolated population of human early stage precursors as disclosed herein includes two or more sub-populations of cells that express one or more of the markers identified in Table 1. In one aspect, two of the markers identified in Table 1 are present, or alternatively three, or alternatively four, or alternatively five, and increasing up to the presence of all markers. In some embodiments, the sub-populations of cells in the early stage precursors as disclosed herein express various combinations of markers identified in Table 1. In some embodiments, the early stage precursors as disclosed herein do not express Lin.

In some embodiments, provided is a method of isolating early stage precursors as disclosed herein from adult human tissue sample. Non-limiting examples of adult human tissue include human peripheral blood, umbilical cord blood, bone marrow, umbilical cord, placenta, adipose tissue, brain, blood vessels, skeletal muscle, skin, teeth, dental pulp, heart, liver, ovarian epithelium, testis, kidney, retina, hair follicles, intestine, lung, spleen, lymph node, thymus, pancreas, bone, ligament, and tendon. In some embodiments, provided is a method of isolating early stage precursors as disclosed herein from human blood sample. Non-limiting examples of human blood sample include human peripheral blood and umbilical cord blood.

In some embodiments, the early stage precursors can be isolated from the adult human tissue sample by any means that allows for isolation of cells. For example, to isolate the early stage precursors from human blood sample, the methods as disclosed herein may include removing at least a portion of the red blood cells from the blood sample, and centrifuging the sample to obtain the pellet that includes the early stage precursors. In another example, the methods as disclosed herein may include retrieving cell suspension from adult human tissue samples (e.g., by digesting the tissue samples and removing undigested tissue) and centrifuging the cell suspension to obtain the pellet that includes the early stage precursors. In other aspects, the methods may include cell sorting and cell isolation methods based on one or more identifying markers. For example, fluorescence-activated cell sorting (FACS) or magnetic-activated cell sorting (MACS) may be used to sort and isolate the early stage precursors. In some embodiments, other methods can be used to isolate the early stage precursors as disclosed herein. Examples of some isolation procedures are provided in EXAMPLE 1, infra.

In one aspect, the method of isolation of human early stage precursors comprises (1) removing at least a portion of red blood cells from a human blood sample; (2) centrifuging the sample at 3,000×g-15,000×g, and (3) obtaining a pellet that comprises the human early stage precursors as disclosed herein. In some aspects, the sample in step (2) may be centrifuged at about 3,000×g, or alternatively at about 3,500×g, or alternatively at about 4,000×g, or alternatively at about 4500×g, or alternatively at about 5,000×g, or alternatively at about 5500×g, or alternatively at about 6,000×g, or alternatively at about 6500×g, or alternatively at about 7,000×g, or alternatively at about 7500×g, or alternatively at about 8,000×g, or alternatively at about 8,500×g, or alternatively at about 9,000×g, or alternatively at about 9,500×g, or alternatively at about 10,000×g, alternatively at about 10,500×g, or alternatively at about 11,000×g, alternatively at about 11,500×g, or alternatively at about 12,000×g, alternatively at about 12,500×g, or alternatively at about 13,000×g, alternatively at about 13,500×g, or alternatively at about 14,000×g, alternatively at about 14,500×g, or alternatively at about 15,000×g.

In some aspects, the method of isolation of human early stage precursors comprises (1) digesting a human tissue sample and removing undigested tissue to obtain a cell suspension; (2) centrifuging the cell suspension at 3,000×g-15,000×g, and (3) obtaining a pellet that comprises the human early stage precursors as disclosed herein. In some aspects, the sample in step (2) may be centrifuged at about 3,000×g, or alternatively at about 3,500×g, or alternatively at about 4,000×g, or alternatively at about 4500×g, or alternatively at about 5,000×g, or alternatively at about 5500×g, or alternatively at about 6,000×g, or alternatively at about 6500×g, or alternatively at about 7,000×g, or alternatively at about 7500×g, or alternatively at about 8,000×g, or alternatively at about 8,500×g, or alternatively at about 9,000×g, or alternatively at about 9,500×g, or alternatively at about 10,000×g, alternatively at about 10,500×g, or alternatively at about 11,000×g, alternatively at about 11,500×g, or alternatively at about 12,000×g, alternatively at about 12,500×g, or alternatively at about 13,000×g, alternatively at about 13,500×g, or alternatively at about 14,000×g, alternatively at about 14,500×g, or alternatively at about 15,000×g.

In some embodiments, provided are methods of isolating a specific enriched population of human early stage precursors based on the specific marker(s) of the early stage precursors. In some embodiments, provided are methods of isolating a heterogenous population of human early stage precursors including multiple sub-populations of cells based on specific marker(s) thereof. For example, the methods may be used to isolate a cell population enriched in CD49f$^+$ cells (e.g., by FACS or MACS). In another example, the methods may be used to isolate a cell population enriched in CD49f$^+$/ABCG2$^-$ cells. In another example, the methods may be used to isolate a cell population enriched in CD49f$^+$/Lin$^-$ cells. In another example, the methods may be used to isolate a cell population enriched in CD49f$^+$/SSEA4$^+$/Lin$^-$ cells. In other embodiments, the methods may be used to isolate a cell population enriched in cells having certain sets of specific markers (e.g., various combinations of markers for identifying early stage precursors as disclosed herein).

In some embodiments, the early stage precursors may be isolated from other sources/tissues so long as the tissue contains viable early stage precursors as disclosed herein. In some embodiments, the early stage precursors may be isolated from a subject at any age. In some embodiments, the early stage precursors may be isolated from a subject at any time. In some embodiments, the early stage precursors can be isolated from animals such as, but not limited to, equine, canine, porcine, bovine, murine, simian, and human.

3. Activation and Development

To promote activation/development of the isolated population of early stage precursors in vitro, an activation/development system has been established.

In some embodiments, the activation/development system includes one or more cells/cell lines selected from primary hepatocytes and hepatic cell lines. Non-limiting examples of the hepatic cell lines include cell lines derived from hepatomas, immortalized hepatocytes, immortal hepatocytes isolated from transgenic animals, hepatocyte/hepatoma hybrid cells, genetically engineered hepatocytes, and hepatic progenitor cells. Non-limiting examples of the cell lines derived from hepatomas include HepG2, HepG2.2.15, HLE, HLF, HuH-7, Hep3B, PLC/PRF-5, SNU182, SNU354, SNU368, SNU387, SNU398, SNU423, SNU449, SNU475, and HepaRG. In one embodiment, the immortalized hepatocytes include hepatocytes generated via transformation with virus genes or oncogenes (e.g., simian virus SV40 large T antigen, c-myc, cH-ras), and hepatocytes generated via transfection using recombinant plasmids. For example, the immortalized hepatocytes may include, but are not limited to THLE-2, THLE-3, L-02 (HL-7702), human hepatocyte lines (HHLs). In one embodiment, the immortal hepatocytes include hepatocytes isolated from transgenic animals expressing viral transforming genes, oncogenes or growth factors. In one embodiment, hepatic cell lines also include hepatocyte/hepatoma hybrid cells generated by fusing hepatocytes and hepatoma cells. In one embodiment, hepatic cell lines also include genetically engineered hepatocytes expressing human drug-metabolizing enzymes. In one embodiment, hepatic cell lines also include hepatic progenitor cells such as oval cells in the liver. In some embodiments, the activation/development system may include other types of cells and/or cell lines. In some aspects, the activation/development system may include at least one, or alternatively at least two, or alternatively at least three, or alternatively at least four of the above-mentioned cells/cell lines.

In one aspect, the activation/development system includes a cell mixture of at least primary hepatocytes and one or more selected from the hepatic cell lines. In another aspect, the activation/development system includes at least one selected from the hepatic cell lines. In another aspect, the activation/development system includes a cell mixture of at least two selected from the hepatic cell lines. In another aspect, the activation/development system includes a cell mixture of at least three selected from the hepatic cell lines. In another aspect, the activation/development system includes a cell mixture of at least primary hepatocytes and HepG2. In another aspect, the activation/development system includes a cell mixture of at least primary hepatocytes, HepG2 and HepaRG. In another aspect, the activation/development system includes a cell mixture of at least HepG2 and HepaRG. In another aspect, the activation/development system includes a cell mixture of at least primary hepatocytes and at least one selected from THLE-2, THLE-3, L-02 (HL-7702), and HHLs. In another aspect, the activation/development system includes a cell mixture of at least one selected from THLE-2, THLE-3, L-02 (HL-7702), and HHLs. In another aspect, the activation/development system includes a cell mixture of at least HepaRG and at least one selected from THLE-2, THLE-3, L-02 (HL-7702), and HHLs. In another aspect, the activation/development system includes a cell mixture of at least primary hepatocytes and HepaRG. In another aspect, the activation/development system includes at least HepaRG. In another aspect, the activation/development system includes at least primary hepatocytes.

In some embodiments, provided herein is a method of promoting activation and development of the early stage precursors in a cell culture. In some embodiments, the method of promoting activation and development of the early stage precursors in a cell culture includes culturing the early stage precursors in a medium that is in contact with or has been conditioned with the cells/cell lines or the cell mixture as disclosed herein.

In one aspect, provided herein is a method of promoting activation and development of the early stage precursors in a coculture system with the cells/cell lines or the cell mixture as disclosed herein. In some embodiments, the coculture system may be prepared using Transwell plates. For example, cells or a cell mixture of the above-mentioned cells/cell lines can be prepared and treated with Mitomycin C to mitotically inactivate the cells. Then the cells/cell mixture can be seeded on the bottom of cell culture plates in a coculture medium. The isolated population of early stage precursors can be seeded on the Transwell membranes to be cocultured with the cells/cell mixture. The coculture medium may include α-MEM medium with 5-50% of FBS (fetal bovine serum). For example, the coculture medium may include α-MEM medium with about 5%, or alternatively about 10%, or alternatively about 15%, or alternatively about 20%, or alternatively about 25%, or alternatively about 30%, or alternatively about 35%, or alternatively about 40%, or alternatively about 45%, or alternatively about 50% of FBS. In another embodiment, the coculture medium may include medium with 5-50% of human serum. In another embodiment, the coculture medium may include medium with 5-50% of serum replacement. In another embodiment, the coculture medium may include medium without serum. In some embodiments, other culture medium may be used in the methods as disclosed herein. Optionally other reagents and factors may be added to the coculture medium.

In another aspect, provided herein is a method of promoting activation and development of the early stage precursors using conditioned medium. In some aspects, the culture medium may be conditioned with the above-mentioned cells/cell lines or the cell mixture before use in the activation/development system. For example, the above-mentioned cells/cell mixture can be suspended in cell culture medium and then seeded in a cell culture dish/plate. The cell culture medium for culturing the cells/cell mixture may include DMEM with 5-50% of FBS. For example, the medium may include DMEM with about 5%, or alternatively about 10%, or alternatively about 15%, or alternatively about 20%, or alternatively about 25%, or alternatively about 30%, or alternatively about 35%, or alternatively about 40%, or alternatively about 45%, or alternatively about 50% of FBS. In another embodiment, the cell culture medium for culturing the cells/cell mixture may include medium with 5-50% of human serum. In another embodiment, the cell culture medium for culturing the cells/cell mixture may include medium with 5-50% of serum replacement. In another embodiment, the cell culture medium for culturing the cells/cell mixture may include medium without serum. In some embodiments, other culture medium may be used in the methods as disclosed herein. Optionally other reagents and factors may be added to the medium. The conditioned medium can be collected from the cell culture dishes/plates, and the remaining cells in the medium can be removed (e.g., via centrifugation and/or filtering) before use of the medium to culture the isolated early stage precursors. In one aspect, the collected conditioned medium may be directly used to culture the isolated early stage precursors as disclosed herein. In another aspect, the collected conditioned medium may be mixed with the above-mentioned cell culture medium, for culturing the early stage precursors. For example, based on the total volume of the medium mixture, the conditioned medium as disclosed herein may be about 5% (v/v), or alternatively about 10%, or alternatively about 15%, or alternatively about 20%, or alternatively about 25%, or alternatively about 30%, or alternatively about 35%, or alternatively about 40%, or alternatively about 45%, or alternatively about 50%, or alternatively about 55%, or alternatively about 60%, or alternatively about 65%, or alternatively about 70%, or alternatively about 75%, or alternatively about 80%, or alternatively about 85%, or alternatively about 90%, or alternatively about 95%, or alternatively about 100%. Optionally other reagents and factors may be added to the mixture of medium.

In some embodiments, the activation/development system includes compositions and/or systems that promote cell fusion. Non-limiting examples of cell fusion include electrical cell fusion (or electrofusion), chemically (e.g., polyethylene glycol, or PEG) mediated cell fusion, virus (e.g., Sendai virus) induced cell fusion, cell fusion driven by mechanical tension (e.g., microinjection), and cell fusion caused by intensive/high-speed centrifugation. In some embodiments, the activation/development system includes compositions and/or systems that promote electrical cell fusion, chemically mediated cell fusion, virus induced cell fusion, mechanical tension driven cell fusion, centrifugation driven cell fusion, or combinations thereof. In some embodiments, any other composition and/or systems that induce cell fusion may be included in the activation/development system as disclosed herein.

In one embodiment, provided herein is a method of promoting activation and development of the early stage precursors in vitro. In some embodiment, the method of promoting activation and development of the early stage precursors incudes promoting cell fusion. In some embodiment, also provided is a method of promoting activation and development of the early stage precursors, including electrical methods that induce cell fusion, chemical methods/treatments (e.g., PEG) that mediate cell fusion, virus (e.g., Sendai virus) induced cell fusion, mechanical methods (e.g., microinjection) that drives cell fusion, high speed centrifugation methods that lead to cell fusion, or combinations thereof.

In some embodiments, the method of promoting activation and development of the early stage precursors includes promoting cell fusion as disclosed herein and culturing the early stage precursors in the medium as disclosed herein concurrently or sequentially. In some embodiments, promoting cell fusion may or may not be necessary for activation and development of the early stage precursors. In some embodiments, the step of promoting cell fusion is optional.

Embodiments of the disclosure also provide a population of activated stem cells derived from the early stage precursors as disclosed herein. The activated stem cells may be obtained by culturing the early stage precursors in the above-mentioned activation/development system for an effective period of time. In some aspects, the culturing time effective for activating the early stage precursors may include, but not limited to, at least 1 hour, or alternatively at least 2 hours, or alternatively at least 4 hours, or alternatively at least 12 hours, or alternatively at least 1 day, or alternatively at least 2 days, or alternatively at least 3 days, or alternatively at least 4 days, or alternatively at least 5 days, or alternatively at least 8 days, or alternatively at least 10 days, or alternatively at least 12 days, or alternatively at least 15 days, or alternatively at least 18 days, or alternatively at least 20 days, or alternatively at least 25 days, or alternatively at least 30 days. The cell culture medium may be changed every 1 day, or alternatively every 2 days, or alternatively every 3 days, or alternatively every 4 days, or alternatively every 5 or more days. In some embodiments, the activated stem cells may be obtained by culturing the early stage precursors in other culture systems, culture medium, or conditions for an effective period of time. In some embodiments, the activated stem cells are characterized as a heterogeneous cell mixture, including various sub-populations of cells characterized by different sets of markers.

In some embodiments, other cell culture mediums and/or cell culture conditions may be used to activate and/or culture the stem cells as disclosed herein. In some embodiments, the cell culture medium and/or cell culture conditions used in the activation/development system as disclosed herein may be used to culture other types of cells and/or other types of stem cells. For example, the cell culture medium and/or cell culture conditions used in the activation/development system may be used to culture one or more of cells selected from the group consisting of embryonic stem (ES) cells, hematopoietic stem cells (HSCs), mesenchymal stem cells (MSCs), endothelial stem cells (ESCs), mammary stem cells (MaSCs), intestinal stem cells (ISCs), neural stem cells (NSCs), adult olfactory stem cells (OSCs), neural crest stem cells (NCSCs), and testicular stem cells (TSCs), and induced pluripotent stem cells (iPSCs).

In some embodiments, the activated stem cells, derived from the early stage precursors, include a population of cells expressing ABCG2, which is not expressed in the early stage precursors. In some aspects, a nucleic acid stain (e.g., Hoechst 33342) is gradually exhausted outside of the activated stem cells cultured in the activation/development system, while the nucleic acid stain in the early stage precursors is not exhausted in a regular cultured medium as disclosed herein.

Also provided herein, in some embodiments, is a population of activated stem cells, derived from the early stage precursors, that are CD49f$^+$/Lin$^-$. In some embodiments, the population of activated stem cells express ABCG2. In some embodiments, the population of activated stem cells express one or more markers selected from the group consisting of CD49f, ABCG2, and SSEA4, and does not express Lin. In some embodiments, the population of activated stem cells express one or more markers selected from the group consisting of CD49f, ABCG2, SSEA4, and Lin28, and does not express Lin. In some embodiments, the population of activated stem cells express one or more markers selected from the group consisting of CD49f, ABCG2, Oct4, Nanog, SSEA4, Lin28, CD44, and CD105. In some embodiments, the population of activated stem cells express one or more markers selected from the group consisting of CD49f, CD73, ABCG2, Oct4, Nanog, SSEA4, and CD105. In some embodiments, the population of activated stem cells express one or more markers selected from the group consisting of Lin28, CD44, CD184, and CD106. In some embodiments, the population of activated stem cells express very low level of CD34. In some embodiments, the population of activated stem cells as disclosed herein express one or more proliferation markers (e.g., Cyclin D1 and c-Myc). In some embodiments, the population of activated stem cells as disclosed herein express one or more cytokines (e.g., VEGF, TGF-β, HGF, IL-6, and IL10). In some embodiments, the population of activated stem cells do not express one or more markers selected from the group consisting of CD117, CD31, CD38, CD45, CD150, CD90, and Lin. In some embodiments, the population of activated stem cells do not express one or more markers selected from the group consisting of CD3, CD4, CD11b, CD14, CD19, CD8, and CD41. In some embodiments, the population of activated stem cells as disclosed herein are HLA-I$^{Low}$/HLA-II$^-$. In some embodiments, the population of activated stem cells express one or more endoderm specific markers, such as albumin and alpha fetal protein (AFP). In some embodiments, the population of activated stem cells express one or more mesoderm specific markers, such as osteocalcin and desmin. In some embodiments, the population of activated stem cells express one or more ectoderm specific markers, such as nestin.

Also provided herein, in some embodiments, is a composition comprising at least 1000 human cells, and at least 40% of the cells are activated stem cells as disclosed herein. In one aspect, the composition comprises at least 2000, or alternatively at least 5000, or alternatively at least 10000, or alternatively at least 50000, or alternatively at least 100000 human cells, and at least 40%, or alternatively at least 50%, or alternatively at least 60%, or alternatively at least 70%, or alternatively at least 80%, or alternatively at least 90%, or alternatively at least 95%, or alternatively at least 98% of the cells are activated stem cells.

In some embodiments, the population of activated stem cells is a heterogenous cell population that includes one or more of sub populations of cells. In some embodiments, one or more of the sub-populations of the activated stem cells as disclosed herein can expand in the activation/development system in vitro. In some embodiments, the doubling time for the sub-populations of the activated stem cells may vary. In some embodiments, the doubling time for one or more of the sub-populations of the activated stem cells in the activation/development system may be more than 80 hours, or alternatively less than 75 hours, or alternatively less than 70 hours, or alternatively less than 65 hours, or alternatively less than 60 hours, or alternatively less than 55 hours, or alternatively less than 50 hours, or alternatively less than 45 hours, or alternatively less than 40 hours, or alternatively less than 35 hours, or alternatively less than 30 hours, or alternatively less than 25 hours, or alternatively less than 20 hours, or alternatively between about 20 and about 80 hours, or alternatively between about 20 and about 75 hours, or alternatively between about 20 and about 70 hours, or alternatively between about 20 and about 65 hours, or alternatively between about 20 and about 60 hours, or alternatively between about 20 and about 55 hours, or alternatively between about 20 and about 50 hours, or alternatively between about 20 and about 40 hours, or alternatively between about 20 and about 30 hours, or alternatively between about 30 and about 75 hours, or alternatively between about 35 and about 75 hours, or alternatively between about 40 and about 75 hours, or alternatively between about 45 and about 75 hours, or alternatively between about 50 and about 75 hours, or alternatively between about 55 and about 75 hours, or alternatively between about 60 and about 75 hours, or alternatively between about 40 and about 70 hours, or alternatively between about 40 and about 65 hours, or alternatively between about 40 and about 60 hours, or alternatively between about 45 and about 70 hours, or alternatively between about 45 and about 65 hours, or alternatively between about 50 and about 70 hours, or alternatively between about 50 and about 65 hours, or alternatively between about 55 and about 65 hours. In some embodiments, one or more of the sub-populations of the activated stem cells can expand in other cell culture systems and/or under other culture conditions in vitro.

Also provided herein are methods for purifying a sub-population of activated stem cells derived from the early stage precursors as disclosed herein. In one aspect, provided is a method for purifying a sub-population of activated stem cells that has a certain set of markers, derived from the early stage precursors as disclosed herein.

In one embodiment, after culturing in the activation/development system for a period of time (e.g., 5-10 days), one or more cell colonies are developed. The early stage precursors cultured in regular medium (e.g., α-MEM medium with 10% FBS) do not grow and expand, and do not develop into cell colonies, in some aspects.

In some embodiments, provided herein are methods for isolating a cell colony derived from the early stage precursors as disclosed herein. For example, a cell colony can be picked up using a cloning cylinder. Alternatively, a cell colony can be isolated by trypsinizing and detaching the colony from the cell culture plate/dish. It should be understood that other methods can also be employed to isolate the cell colonies.

Also provided herein are methods for purifying a population of activated stem cells from the isolated colonies as disclosed herein. In some embodiments, methods such as MACS or FACS can be used to purify a specific population or an enriched cell population from the activated stem cells. In some embodiments, other methods can be used to purify a specific population or an enriched cell population from the activated stem cells.

4. Differentiation of the Activated Stem Cells

The activated stem cell population and/or various sub-populations therein, derived from the early stage precursors as disclosed herein, can be identified by their pluripotency, e.g., the capacity to differentiate into cell types from all three germ layers (ectoderm, mesoderm, and endoderm) using the appropriate culture conditions and medium. Confirmation of the differentiation state of the cells can be performed by identification of cell type specific markers as known to those of skill in the art.

The present disclosure provides methods of inducing differentiation of the activated stem cell population, derived from the early stage precursors as disclosed herein, into ectodermal lineage. Also provided are compositions or populations of differentiated cells in ectodermal lineage, derived from the activated stem cell population that are derived from the early stage precursors as disclosed herein. In one aspect, the activated stem cells are capable of differentiation into at least one of the cell types in the ectodermal lineage. In another aspect, the activated stem cells are capable of differentiation into at least two, at least three, and increasing up to all of the cell types in the ectodermal lineage. Non-limiting examples of cells that differentiate into ectodermal lineage include, but are not limited to epithelial cells, neurogenic cells, and neurogliagenic cells.

In other aspects, also provided are methods of inducing differentiation of various sub-populations in the activated stem cell population, which are derived from the early stage precursors as disclosed herein, into ectodermal lineage. Also provided are compositions or populations of differentiated cells in ectodermal lineage, derived from various sub-populations in the activated stem cell population, derived from the early stage precursors as disclosed herein. In other aspects, also provided are methods of inducing differentiation of the sub-populations of the activated stem cells as disclosed herein into ectodermal lineage. Also provided are compositions or populations of differentiated cells in ectodermal lineage, derived from the sub-populations of the activated stem cells as disclosed herein.

The present disclosure also provides methods of inducing differentiation of the activated stem cell population, which are derived from the early stage precursors as disclosed herein, into mesodermal lineage. Also provided are compositions or populations of differentiated cells in mesodermal lineage, derived from the activated stem cell population that is derived from the early stage precursors as disclosed herein. In another aspect, the activated stem cells are capable of differentiation into at least one of the cell types in the mesodermal lineage. In another aspect, the activated stem cells are capable of differentiation into at least two, or alternatively at least three, or alternatively at least four, and increasing up to all of the cell types in the mesodermal lineage. Non-limiting examples of cells that differentiate into mesodermal lineage include, but are not limited to adipogenic, leiomyogenic, chondrogenic, cardiogenic, dermatogenic, hematopoetic, hemangiogenic, myogenic, nephrogenic, urogenitogenic, osteogenic, pericardiogenic, or stromal cells.

In other aspects, also provided are methods of inducing differentiation of various sub-populations in the activated stem cell population, which are derived from the early stage precursors as disclosed herein, into mesodermal lineage. Also provided are compositions or populations of differentiated cells in mesodermal lineage, derived from various sub-populations in the activated stem cell population, derived from the early stage precursors as disclosed herein. In other aspects, also provided are methods of inducing differentiation of the sub-populations of the activated stem cells as disclosed herein into mesodermal lineage. Also provided are compositions or populations of differentiated cells in mesodermal lineage, derived from the sub-populations of the activated stem cells as disclosed herein.

The present disclosure also provides methods of inducing differentiation of the activated stem cell population, derived from the early stage precursors as disclosed herein, into endodermal lineage. Also provided are compositions or populations of differentiated cells in endodermal lineage, derived from the activated stem cell population that is derived from the early stage precursors as disclosed herein. In one aspect, the activated stem cells are capable of differentiation into at least one of the cell types in the endodermal lineage. In another aspect, the activated stem cells are capable of differentiation into at least two, or alternatively at least three, or alternatively at least four, or alternatively at least five, and increasing up to all of the cell types in the endodermal lineage. Non-limiting examples of cells that differentiate into endodermal lineage include, but are not limited to cells in the pancreas, liver, lung, stomach, intestine, and thyroid.

In other aspects, also provided are methods of inducing differentiation of various sub-populations in the activated stem cell population, derived from the early stage precursors as disclosed herein, into endodermal lineage. Also provided are compositions or populations of differentiated cells in endodermal lineage, derived from various sub-populations in the activated stem cell population, derived from the early stage precursors as disclosed herein. In other aspects, also provided are methods of inducing differentiation of the sub-populations of the activated stem cells as disclosed herein into endodermal lineage. Also provided are compositions or populations of differentiated cells in endodermal lineage, derived from the sub-populations of the activated stem cells as disclosed herein.

5. Method of Use

The present disclosure provides methods of treating diseases in a subject in need thereof using the activated stem cells that are derived from the early stage precursors as disclosed herein. In some embodiments, provided are methods of treating diseases in a subject in need thereof using one or more sub-populations in the activated stem cell population, derived from the early stage precursors as disclosed herein. In some embodiments, provided are methods of treating diseases in a subject in need thereof using differentiated cells, derived from the activated stem cells that are derived from the early stage precursors as disclosed herein. Regenerative medicine includes therapies designed to aid the repair, replacement, or regeneration of damaged cells, tissues, or organs. The methods as disclosed herein may be used in cell-based therapies in the regenerative medicine.

In some aspects, the methods and compositions disclosed herein may be used to treat diseases or conditions such as degenerative diseases, proliferative disorders, hereditary diseases, injuries, and/or organ failures. Non-limiting examples of the diseases or conditions include neurodegenerative disorders; neurological disorders such as cognitive impairment, and mood disorders; auditory disease such as deafness; osteoporosis; cardiovascular diseases; diabetes; metabolic disorders; respiratory diseases; drug sensitivity conditions; eye diseases such as macular degeneration; immunological disorders; hematological diseases; kidney diseases; proliferative disorders; genetic disorders, traumatic injury, stroke, organ failure, or loss of limb. Other examples of the diseases include a neurodegenerative disorder, a neurological disorder, an eye disease, a mood disorder, a respiratory disease, an auditory disease, a cardiovascular disease, an immunological disorder, a hematological disease, a metabolic disorder, a kidney disease, a proliferative disorder, a genetic disorder, an autoimmune disease, a drug sensitivity condition, a cognitive impairment, depression, deafness, osteoporosis, diabetes, macular degeneration, obesity, Alexander's disease, Alper's disease, Alzheimer's disease, amyotrophic lateral sclerosis, ataxia telangiectasia, Batten disease, Canavan disease, Cockayne syndrome, corticobasal degeneration, Creutzfeldt-Jakob disease, Huntington's disease, HIV-associated dementia, Kennedy's disease, Krabbe's disease, lewy body dementia, Machado-Joseph disease, multiple sclerosis, multiple system atrophy, narcolepsy, neuroborreliosis, Parkinson's disease, Pelizaeus-Merzbacher Disease, Pick's disease, primary lateral sclerosis, a prion disease, Refsum's disease, Sandhoffs disease, Schilder's disease, subacute combined degeneration of spinal cord secondary to pernicious anaemia, schizophrenia, spinocerebellar ataxia, spinal muscular atrophy (SMA), Steele-Richardson-Olszewski disease, tabes dorsalis, acquired immune deficiency, leukemia, lymphoma, a hypersensitivity (allergy), severe combined immune deficiency, acute disseminated encephalomyelitis, addison's disease, ankylosing spondylitis, antiphospholipid antibody syndrome, autoimmune hemolytic anemia, autoimmune hepatitis, bullous pemphigoid, coeliac disease, dermatomyositis, diabetes mellitus type 1, diabetes mellitus type 2, Goodpasture's syndrome, Graves' disease, Guillain-Barre syndrome, Hashimoto's disease, idiopathic thrombocytopenic purpura, lupus erythematosus, myasthenia gravis, pemphigus, pernicious anaemia, polymyositis, primary biliary cirrhosis, rheumatoid arthritis, Sjogren's syndrome, temporal arthritis, vasculitis, Wegener's granulomatosis, aneurysm, angina, arrhythmia, atherosclerosis, cardiomyopathy, calcific aortic valve disease (CAVD), cerebrovascular accident (stroke), cerebrovascular disease, congenital heart disease, congestive heart failure, myocarditis, valve disease coronary, cardiomyopathy, diastolic dysfunction, endocarditis, hypertension, hypertrophic cardiomyopathy, mitral valve prolapse, myocardial infarction, venous thromboembolism, acid lipase disease, amyloidosis, Barth Syndrome, biotinidase deficiency, camitine palmitoyl transferase deficiency type II, central pontine myelinolysis, muscular dystrophy, Farber's Disease, glucose-6-phosphate dehydrogenase deficiency, gangliosidoses, trimethylaminuria, Lesch-Nyhan syndrome, lipid storage diseases, metabolic myopathies, methylmalonic aciduria, mitochondrial myopathies, mucolipidoses, mucopolysaccharidoses, mucolipidoses, mucopolysaccharidoses, multiple CoA carboxylase deficiency, nonketotic hyperglycinemia, Pompe disease, propionic acidemia, type I glycogen storage disease, urea cycle disorders, hyperoxaluria, oxalosis, carcinoma, sarcoma, germ cell tumors, blastic tumors, prostate cancer, lung cancer, colorectal cancer, bladder cancer, cutaneous melanoma, breast cancer, endometrial cancer, and ovarian cancer.

In one aspect, provided are methods of treating skin wounds in a subject in need thereof using the activated stem cells or differentiated cells derived therefrom as disclosed herein. In one aspect, provided are methods of treating liver damages in a subject in need thereof using the activated stem cells or differentiated cells derived therefrom as disclosed herein. In one aspect, provided are methods of treating bone damages or conditions (e.g., arthritis, osteoporosis, etc.) in a subject in need thereof using the activated stem cells or differentiated cells derived therefrom as disclosed herein. In one aspect, provided are methods of treating nerve injuries or neuron degenerative diseases in a subject in need thereof using the activated stem cells or differentiated cells derived therefrom as disclosed herein. In one aspect, provided are methods of treating heart tissue damages or heart failure in a subject in need thereof using the activated stem cells or differentiated cells derived therefrom as disclosed herein. In one aspect, provided are methods of treating chronic diseases such as diabetes in a subject in need thereof using the activated stem cells or differentiated cells derived therefrom as disclosed herein.

In one aspect, provided are methods of autologous transfer of the activated or differentiated cells as disclosed herein. In one aspect, provided are methods of allogeneic transfer of the activated or differentiated cells as disclosed herein. In one aspect, provided are methods of syngeneic transfer of the activated or differentiated cells as disclosed herein.

EXAMPLES

Example 1

Isolation of Early Stage Precursors from Adult Human Tissue

The following method was used to isolate early stage precursors from adult human tissues. Tested adult human tissue included human peripheral blood, umbilical cord blood, bone marrow, and umbilical cord, et al. In one experiment, human peripheral blood was collected at the Stanford Blood Center, Stanford CA. All blood donors provided written informed consent. 5-10 ml of human peripheral blood was collected in Lithium-heparin tubes (BD diagnostics) and kept at 4° C. In another experiment, umbilical cord blood was collected during obstetrical delivery and kept at 4° C. Cord tissues were also collected and kept at 4° C. In another experiment, bone marrow was collected for the isolation of human early stage precursors. Other human tissue samples were successfully used.

The following method was used to isolate early stage precursors from blood samples such as peripheral blood and umbilical cord blood. To lyse the red blood cells (RBC), the collected blood sample was mixed with RBC lysis buffer for human (Alfa Aesar) at a ratio of 1:10, and incubated at room temperature for 5 minutes. The suspension was then centrifuged at 3,000-15,000×g for 40 minutes at 4° C. The pellet was washed and resuspended in 5 ml of 1×PBS, and then was centrifuged at 3,000-15,000×g for 40 minutes at 4° C. The supernatant was removed, and the pellet that contained early stage precursors was resuspended in 5 ml of PBS or culture medium (e.g., α-MEM with 10% FBS) for further analysis, or was cultured in an activation/development system as described below in EXAMPLE 2.

Figure 2:
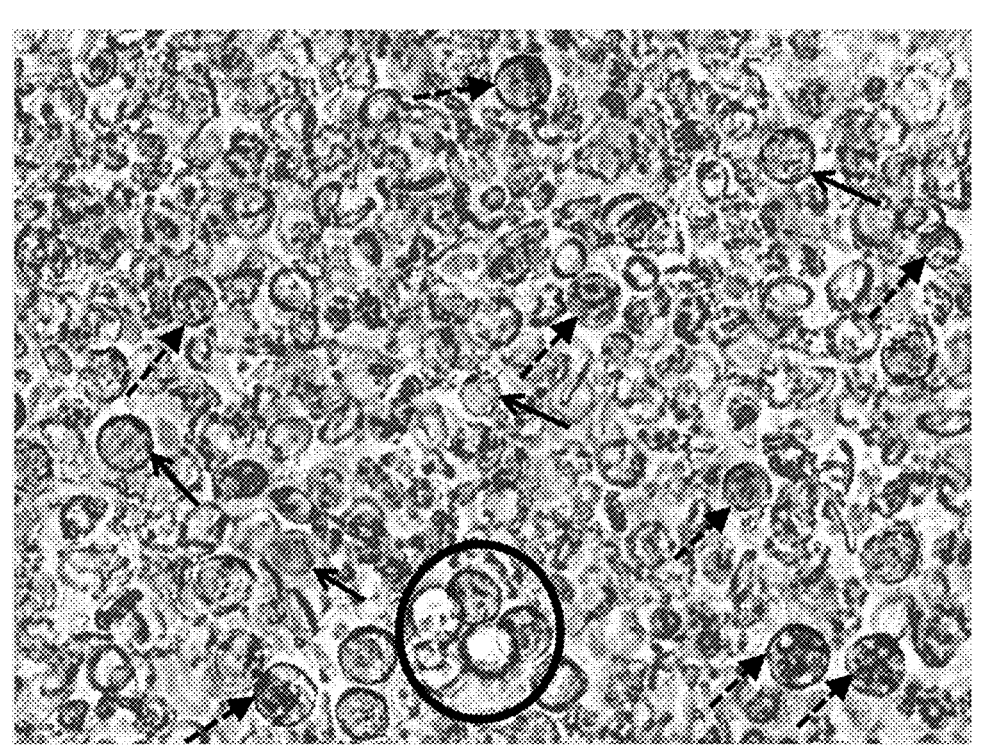
FIG. 2 shows nucleus staining of the early stage precursors after seeded in an activation/development system.

The resuspended pellet contained an enriched population of relatively small cells having an average diameter below 6 µm (FIG. 1). As demonstrated below, at least a large proportion of these cells are early stage precursors. Hoechst 33342 staining showed that these isolated early stage precursors had a very high nucleus-cytoplasm ratio (FIG. 2, dotted arrows). When cultured in the activation/development system for 1 day, the Hoechst 33342 nucleic acid staining diffused outside of the cell membrane in some of the early stage precursors (FIG. 2, solid arrows). Some of the isolated early stage precursors clustered, appearing to fuse with another (FIG. 2, circled). Immunofluorescence (IF) and fluorescence-activated cell sorting (FACS) analysis were used to examine cell markers expressed by the early stage markers. The results showed that the enriched small cell populations included a heterogeneous mixture of cells. The majority of the cells capable of activation expressed CD49f, CD73, CD31, SSEA4, CD117, Oct4, Nanog, CD45, CD105, and very low level of CD34. Markers that were surveyed but were not detected on these cells included ABCG2 (a marker of activated precursor cells) and Lin (hematolymphoid lineage markers), as well as CD90, Lin28, CD3, CD4, CD8, CD11b, CD14, CD19, and CD41.

The early stage precursors were further purified or enriched from the cell pellets. CD49f$^+$ cell fractions were enriched by MACS or FACS following the protocol recommended by the manufacturer (Miltenyi Biotec Inc. San Diego, CA). The enriched cell population was then prepared for further analysis or activation/development system. In another approach, the isolated population of relatively small cells including early stage precursors were cultured in the activation/development system followed by enrichment/purification.

Example 2

Activation/Development of Early Stage Precursors In Vitro

The following method was used to promote activation/development of the early stage precursors obtained from adult human tissue as described in EXAMPLE 1 above. An activation/development system was developed to activate and culture the human early stage precursors in vitro.

Cell Fusion

Cell fusion was observed during culturing of the population of relatively small cells including early stage precursors obtained from adult human tissues. The cell pellet that included human early stage precursors was gently resuspended in 1 ml of 50% PEG 1500 and incubated for 2 minutes at room temperature. Then 1 ml of serum-free α-MEM was added slowly and the cells were incubated at room temperature for 30 minutes. The suspension was then centrifuged at 3,000-15,000×g for 10 minutes at 4° C. The supernatant was removed and the cell pellet was gently resuspended and cultured in the activation/development system.

Other cell fusion methods tested included electrical cell fusion (or electrofusion), virus (e.g., Sendai virus) induced cell fusion, cell fusion driven by mechanical tension (e.g., microinjection), and/or cell fusion caused by intensive/high-speed centrifugation.

Activation/Development In Vitro

To promote activation/development of the early stage precursors in cell culture, an activation/development system was prepared. The system employed a medium that included cells, or mixtures of cells of primary hepatocytes and/or hepatic cell lines, and other reagents and factors. The activation/development system may be a co-culture system using Transwells, or may use conditioned medium, as described below.

In the coculture system, cells (primary hepatocytes or cultured hepatic cell lines, or a cell mixture) were treated with Mitomycin C for 2 hours to mitotically inactivate the cells. The cells were then inoculated on 6-well plates in DMEM/F12 with 10% FBS. About sixteen hours after inoculation, the cells adhered to the wells and were approximately 80% confluent. Then the isolated early stage precursors were placed into the upper chamber of a Transwell (24-mm insert, Corning, Corning, New York), to be co-cultured with the above-mentioned cells in a coculture medium of α-MEM with 10% FBS. The isolated early stage precursors were separated from the inactivated cells by the Transwell membrane (0.4 μm pore size). The same culture medium was used and changed every other day for both upper and lower chambers, for about 10 to 20 days.

In a different approach, cell culture medium was conditioned with primary hepatocytes or cultured hepatic cell lines, or a mixture. The cells were suspended in DMEM medium with 10% FBS or human serum and then seeded in a cell culture dish. The medium was collected from the cell culture dish every 2 days, and then new medium was added to the cell culture dish until the cells reached 100% confluence. The medium collected at different time can be mixed together, and can be stored at −20° C. for short term storage or at −80° C. for long term storage. Before use, the conditioned medium was centrifuged at 3000×g to pellet the remaining cells in the medium. The conditioned medium can also be filtered with the 0.22 μm filter to remove the remaining cells. Then the conditioned medium was mixed with regular cultural medium (e.g., α-MEM with 10% FBS or human serum) in a ratio (v/v) of about 1:3 to about 3:1. In another experiment, the conditioned medium was used directly without mixing to culture the isolated early stage precursors. The isolated early stage precursors were gently resuspended in the above-mentioned medium, and then were seeded in culture dishes or plates. The medium was changed every other day. The cell culture was observed every day under microscope for cell growth and formation of cell colonies. Cell colonies were picked and stem cells were purified for further analysis, e.g., using immunofluorescence staining and FACS analysis.

Figure 3:
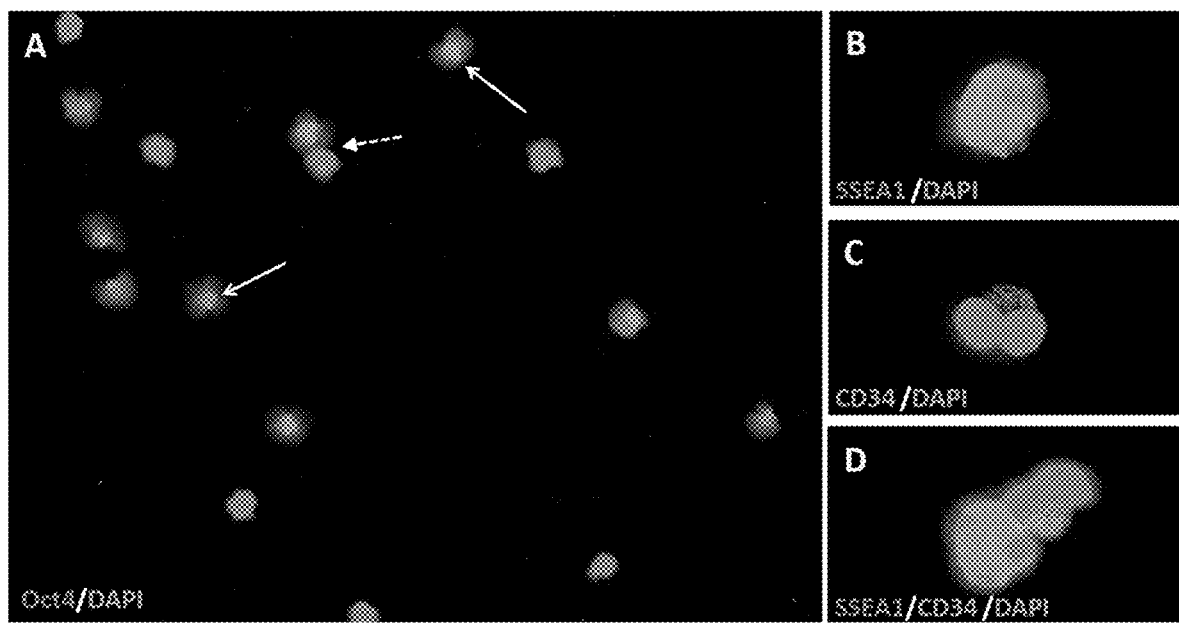
FIG. 3 shows expression of early stage markers in the early stage precursors being cultured in the activation/development system.

Immunofluorescent (IF) staining results showed cell fusion between some of the early stage precursors, observed at 12 days after being cultured in the activation/development system. Cell fusions were observed between the relatively small cells including early stage precursors expressing Oct4 (FIG. 3A, solid arrow) and between Oct4$^+$ and Oct4$^−$ cell (FIG. 3A, dotted arrow). Cells that fused also expressed SSEA1 (FIGS. 3B and 3D) and CD34 (FIG. 3C-D).

The activated stem cells, after being cultured in the above-mentioned activation/development system for 4 weeks, were studied for expression of markers. The results showed that the activated stem cells, derived from the early stage precursors of EXAMPLE 1 expressed CD49f, CD73, CD105, Oct4, Nanog, SSEA4, and ABCG2. The activated cells also expressed Lin28, CD44, CD184, and CD106, and a low level of CD34. These activated stem cells did not express Lin, CD117, CD31, CD38, CD45, CD150, CD90, CD3, CD4, CD11b, CD14, CD19, CD8, or CD41.

Figure 4:
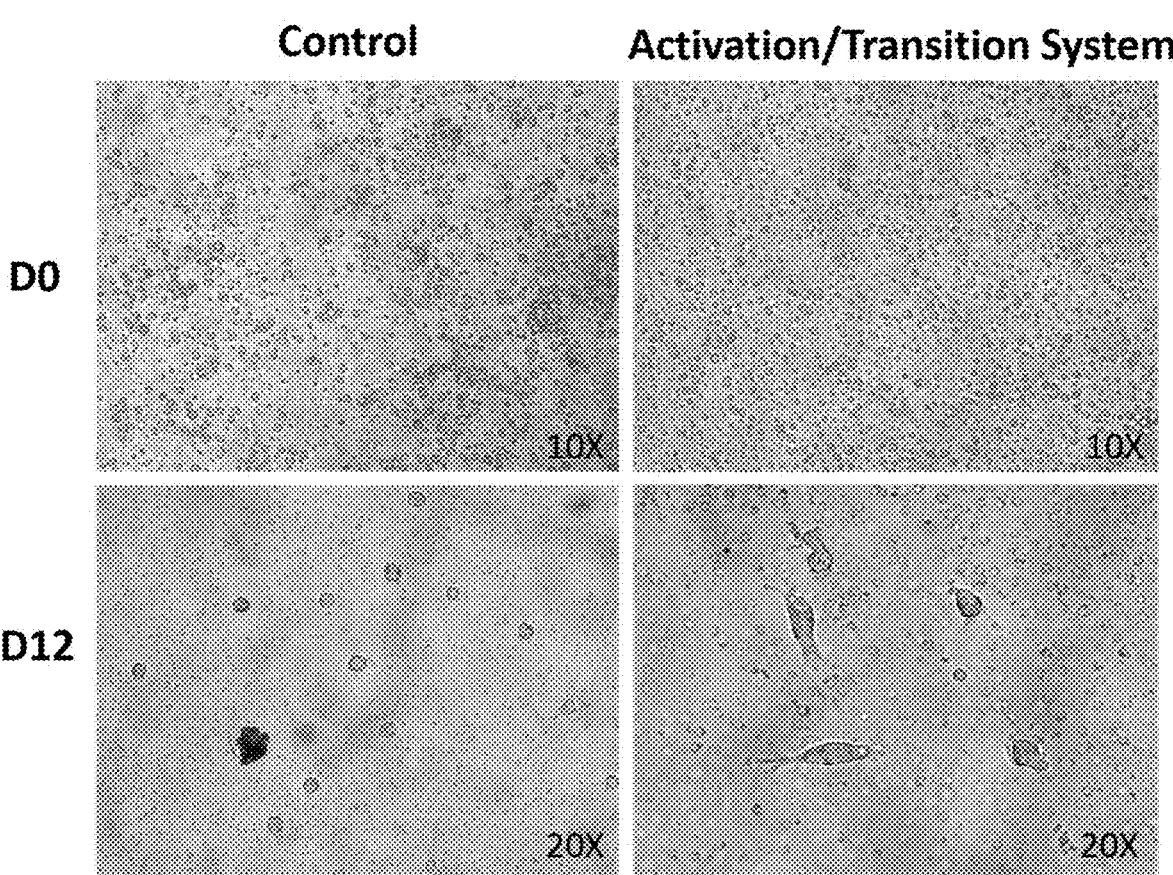
FIG. 4 shows growth and expansion of the early stage precursors in the activation/development system.
Figure 5:
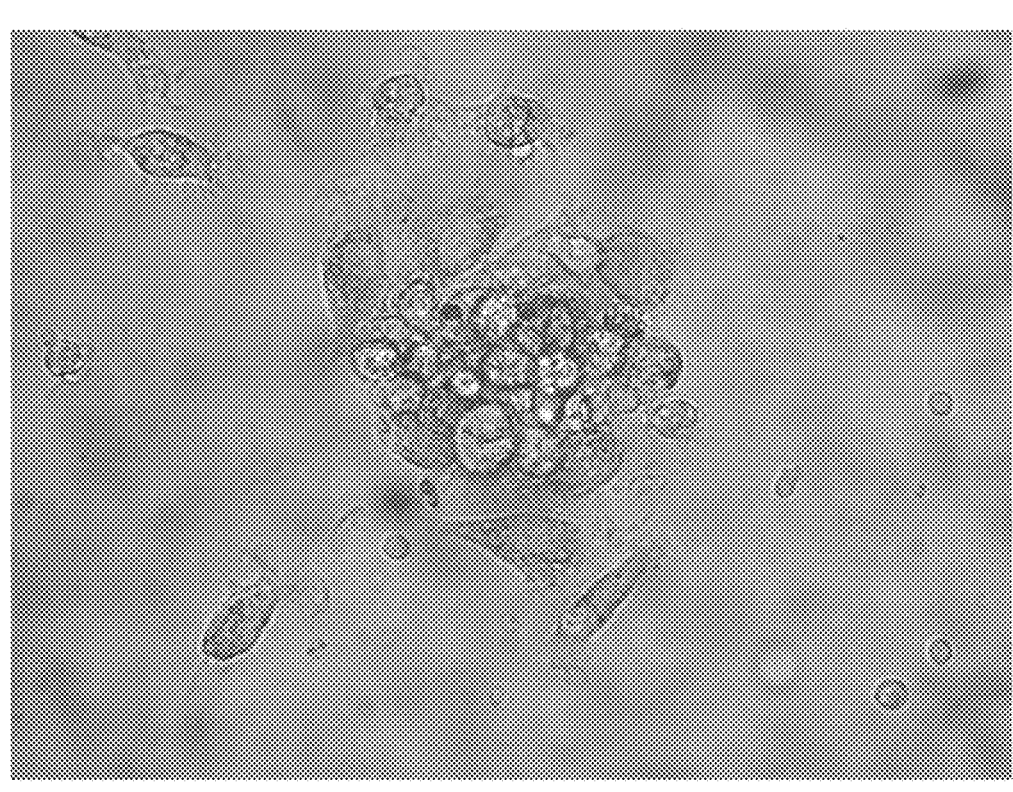
FIG. 5 shows formation of stem cell colonies, derived from the early stage precursors, in the activation/development system.

After being cultured in the activation/development system for 12 days, the activated stem cells became larger than the early stage precursors and changed in the shape (FIG. 4). The early stage precursors cultured in the regular medium (e.g., α-MEM with 10% FBS) did not grow (FIG. 4). Cell colonies derived from the early stage precursors were observed in the activation/development system (see a cell colony at Day 5 as shown in FIG. 5). The activated stem cells were CD49f$^+$ and were further purified from the colonies.

Example 3

Expression of Proliferation Markers, Growth Factors, and Cytokines

The following method was used to assess the expression levels of proliferation markers, growth factors, and cytokines in the activated stem cells as described in EXAMPLE 2 above. RT-PCR was performed to detect the expression levels of proliferation markers including Cyclin D-1 and c-Myc, and growth factors and cytokines including transforming growth factor beta (TGF-β), vascular endothelial growth factor (VEGF), hepatocyte growth factor (HGF), IL-6, and IL10. GAPDH was used as an internal control. The levels of growth factors and cytokines were also evaluated by IF and other methods. The results showed that the population of activated stem cells expressed proliferation markers Cyclin D1 and c-Myc and growth factors and cytokines including VEGF, TGF-β, HGF, IL-6, and IL10. The activated stem cells were HLA-I$^{Low}$/HLA-II$^−$, indicating low immunogenicity. The results further showed that the population of activated stem cells expressed albumin and AFP (endoderm specific markers), osteocalcin and desmin (mesoderm specific markers), and nestin (an ectoderm specific marker), demonstrating potential of pluripotency of the activated stem cells.

Example 4

Treatment of Skin Wounds

The following method was used to treat skin wounds using a population of the activated stem cells prepared in EXAMPLE 2.

Preparation of the Fibrin Gel Scaffold and the 3-D Construct

Fibrin gels were fabricated by thawing stock solutions of fibrinogen and thrombin and mixing together at final concentration of fibrinogen at 12.5 mg/ml and thrombin at 2.5 U/ml plus CaCl$_2$ (final concentration: 45 mM) in a 1.5 ml tube. 200 μl of the mixture was gently pipetted into a 24-well plate. The fibrinogen contents were allowed to form fibrin gel scaffolds for 2 hours at 37° C. The activated stem cells as prepared in EXAMPLE 2 were seeded at 2.5×10$^5$ on the top of fibrin gel scaffolds per well on the 24-well or 48-well plate, and were then cultured in the conditioned medium with 0.5 or 1 ml per well overnight. The cell/scaffold 3-D constructs were then ready for transplantation. In another method, the activated stem cells were pre-mixed with fibrinogen, thrombin and conditioned medium, and then seeded into 24-well or 48-well plates. After fibrin gel formation (e.g., in about two hours), 0.5 or 1 ml of the conditioned medium was added to each well and the cell/scaffold 3-D constructs were cultured overnight and would be ready for transplantation. Before experiments, flow cytometry was also performed to characterize the cultured cells in the cell/scaffold 3-D constructs.

Treatment of Full-Thickness Skin Wounds

After skin preparation, ten immunodeficient (nude) male mice (Simonsen Labs) aged 10-12 weeks received 6 mm in diameter full-thickness punch biopsy wounds on the mid dorsal skin under isoflurane anesthesia. To inhibit wound contraction, a donut shaped splints (inner diameter of 10 mm, outer diameter of 14 mm) fabricated from 1.6 mm thick silicone sheet (Press-to-Seal Silicone Sheet JTR-S-2.0, Grace Bio-Labs, Bend, OR) were placed around the wound area and fixed with eight interrupted sutures using 6-0 nylon sutures (6-0 Ethilon Nylon Suture, Ethicon LLC., Cornelia, GA). Then the above-mentioned cell/scaffold 3-D constructs (about 250,000 cells/construct) were transplanted into the wound bed (n=5). The fibrin gel without stem cells (scaffold only) was also transplanted into the wound bed as control (n=5). A trimmed sterile Tegaderm transparent film dressing (3M) was attached on top of the splint to cover the wound.

Skin Wound Healing Analysis

Photographic images of wounds were taken every day after generation of wound using a digital camera from a fixed distance. To have a gross evaluation of the wound area, the wound area was analyzed by calculating the percentage of the current wound with respect to the original wound area. The wound was considered to be completely closed when the wound area was grossly equal to zero.

The mice were euthanized by $CO_2$ at day D20 post treatment. The skin wound area and the adjacent tissues (about 2.5 cm) were harvested and fixed in 10% (v/v) buffered formaldehyde for more than 16 hours at 4° C. or passed snap-frozen in liquid nitrogen then process to paraffin embedding or frozen section. Specimens were sliced into 5 μm-thick sections and were stained with hematoxylin and eosin (H&E) to examine local cell degeneration and inflammation. Masson's trichrome collagen staining was performed to assess tissue fibrosis in wound regions. The histological parameters considered were wound closure rate, re-epithelialization, dermal regeneration, fibrous deposition, and inflammation. Regeneration of skin appendages was assessed by counting the number of hair follicles or sebaceous glands in the wound bed. Some paraffin skin sections (5 μm) were further processed for immunohistochemistry (IHC) or immunofluorescence (IF).

The images were analyzed to calculate percentage of wound closure rate, percentage of scar area using ImageJ software. Collagen deposit analysis was based on red color region (cellular structure area) divided by blue color region (collagen deposit). Statistical analysis was performed using a paired, two-tailed, Student's t test to compare 2 groups. A value of p<0.05 was considered statistically significant.

Treatment of Diabetic Skin Wounds

Diabetic mice (db/db, Jackson Labs) were used to study the wound healing effect of the above-mentioned cell/scaffold 3-D constructs. After skin preparation, ten diabetic mice aged over 6 months (body weight 60-80 g) were used to create chronic wound on the mid dorsal skin under isoflurane anesthesia. Then the above-mentioned cell/scaffold 3-D constructs (about 250,000 cells/construct) was transplanted into the wound bed (n=5). The fibrin gel without stem cells (scaffold only) was also transplanted into the wound bed as control (n=5). Photographic images of wounds were taken every day after generation of wound and were evaluated as discussed above. The diabetic mice were euthanized by $CO_2$ at day 65 (D65) post treatment. The skin wound area and the adjacent tissues were collected for histological analysis and assessment of therapeutic efficacy as discussed above.

Results

To study the therapeutic potential of these activated stem cells as prepared in EXAMPLE 2 in wound healing, a 3-D cell/scaffold construct was created and applied into a full thickness skin wound on immunodeficient mice. The activated stem cells seeded on the premade fibrin gel (or premixed in the fibrin gel) and cultured overnight before transplantation showed that the cells were growing robustly and to be confluent on the fibrin gel.

Figure 6:
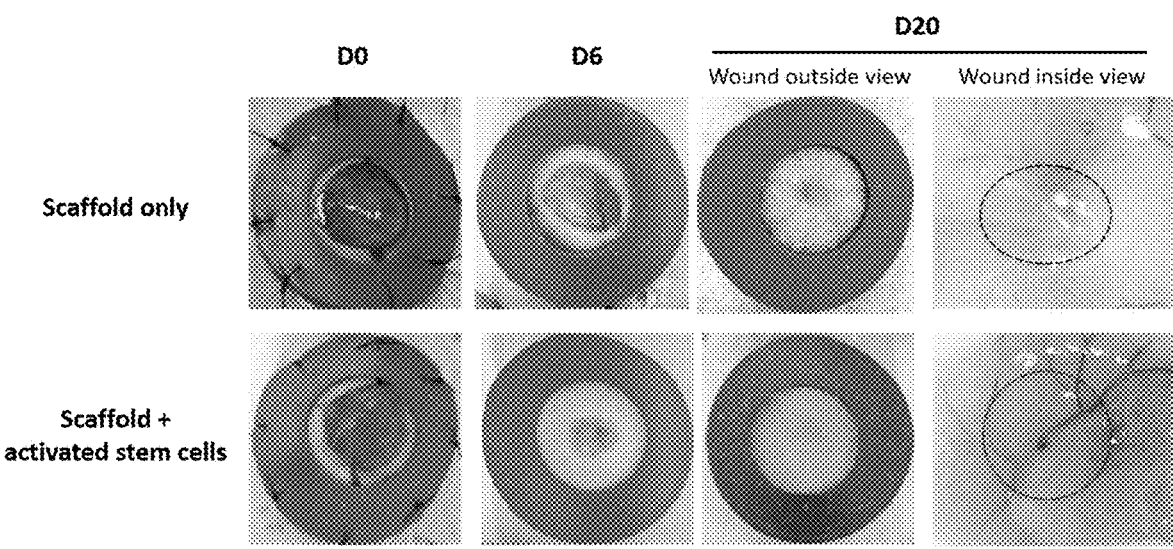
FIG. 6 shows that accelerated wound healing in immunodeficient mice when treated with activated stem cells derived from human early stage precursors.

The treated group (with the cell/scaffold 3-D constructs) exhibited significantly reduced closure time, scar area, and enhanced angiogenesis inside the wound bed (FIG. 6). Morphological image analysis revealed that the treatment with the 3-D construct significantly improved the wound recovery as early as day 5 post wounding and became more evident on day 6. Cumulative image analysis revealed a statistically significant improvement in wound healing after treatment compared to the control group. All wounds treated with the 3-D constructs had closed on day 10 while the wounds in the control group still had opening till day 15.

Histological evaluation revealed enhanced re-epithelialization in the wounds of animals in the treatment group compared to the control group at last day of sacrifice (day 20). The wound surface area or scar region was significantly smaller compared to the control group. The skin of all treated animals showed nearly normal histological structure of the epidermis and dermis.

In the diabetic skin wound model, the results showed accelerated healing of the wounds in the diabetic mice treated with the cell/scaffold 3-D constructs. Histological evaluation revealed enhanced re-epithelialization and recovery of skin structure in the wounds of the mice in the treatment group compared to the control group at last day of sacrifice. In comparison, the wounds in the control group were only closed by a keratinized epidermal layer without subcutaneous tissues and muscle tissue.

What is claimed is:

1. A method for culturing human cells that (a) have a diameter of less than 6 μm, and (b) express CD49f, comprising culturing the human cells in a medium that is in contact with or has been conditioned with primary hepatocytes and a hepatic cell line.

2. The method of claim 1, wherein the human cells are obtained from human blood, express CD49f and CD117, and do not express CD90 and ABCG2.

3. The method of claim 1, wherein the human cells further express SSEA4.

4. The method of claim 1, wherein the human cells do not express Lin.

5. The method of claim 1, wherein the human cells further express Oct4 and do not express Lin28.

6. The method of claim 1, wherein the human cells further express CD45 and do not express CD4.

7. The method of claim 1, wherein the human cells further express CD105.

8. The method of claim 1, wherein the human cells do not express CD3, CD8, CD11b, and CD41.

9. The method of claim 1, wherein the human cells, following the culturing, express ABCG2.

10. The method of claim 1, wherein the culturing is at least for one hour.

11. The method of claim 1, wherein the hepatic cell line is derived from hepatomas, immortalized hepatocytes, immortal hepatocytes isolated from transgenic animals, hepatocyte/hepatoma hybrid cells, genetically engineered hepatocytes, hepatic progenitor cells, or the combination thereof.

12. The method of claim 1, wherein the hepatic cell line is selected from the group consisting of HepG2, HepG2.2.15, HLE, HLF, HuH-7, Hep3B, PLC/PRF-5, SNU182, SNU354, SNU368, SNU387, SNU398, SNU423, SNU449, SNU475, and HepaRG.

13. The method of claim 1, wherein the medium is in contact with or has been conditioned with at least primary hepatocytes.

14. The method of claim 1, wherein the medium is in contact with or has been conditioned with at least the hepatic cell line.

15. The method of claim 1, wherein the medium is in contact with or has been conditioned with both primary hepatocytes and the hepatic cell line.

16. The method of claim 15, wherein the medium is in contact with or has been conditioned with primary hepatocytes and the hepatic cell line concurrently or sequentially.

17. A population of cells obtainable from the method of claim 1.

\* \* \* \* \*